(12) United States Patent
Nishida et al.

(10) Patent No.: US 9,380,968 B2
(45) Date of Patent: Jul. 5, 2016

(54) LIGHT ABSORPTION COEFFICIENT DISTRIBUTION ESTIMATION DEVICE, CONCENTRATION MEASUREMENT DEVICE, AND METHOD FOR CONTROLLING LIGHT ABSORPTION COEFFICIENT DISTRIBUTION ESTIMATION DEVICE

(71) Applicants: SEIKO EPSON CORPORATION, Tokyo (JP); NATIONAL UNIVERSITY CORPORATION HOKKAIDO UNIVERSITY, Sapporo, Hokkaido (JP)

(72) Inventors: Kazuhiro Nishida, Nagano (JP); Koichi Shimizu, Hokkaido (JP); Yuji Kato, Hokkaido (JP)

(73) Assignee: Seiko Epson Corporation, Tokyo (JP)

(*) Notice: Subject to any disclaimer, the term of this patent is extended or adjusted under 35 U.S.C. 154(b) by 298 days.

(21) Appl. No.: 13/935,748

(22) Filed: Jul. 5, 2013

(65) Prior Publication Data
US 2014/0012103 A1    Jan. 9, 2014

(30) Foreign Application Priority Data
Jul. 9, 2012    (JP) .................................. 2012-153552

(51) Int. Cl.
*A61B 5/1455*    (2006.01)
*A61B 5/145*    (2006.01)

(52) U.S. Cl.
CPC .......... *A61B 5/1455* (2013.01); *A61B 5/14532* (2013.01); *A61B 2562/046* (2013.01)

(58) Field of Classification Search
CPC ................................................... A61B 5/1455
See application file for complete search history.

(56) References Cited

U.S. PATENT DOCUMENTS 5,517,987 A    5/1996 Tsuchiya
6,662,030 B2    12/2003 Khalil et al.
(Continued)

FOREIGN PATENT DOCUMENTS

JP    07-049304 A    2/1995
JP    2002-515277 A    5/2002
(Continued)

OTHER PUBLICATIONS

Sugiyama et al.; Development of Accurate Estimation Technique for Absorption Distribution by Time-resolved Measurement of Backscattered Light; IEICE Technical Report; MBE 2011-109-PBE2011-150; ME and Bio Cybernetics; Mar. 14-16, 2012; pp. 25-30.

*Primary Examiner* — Tse Chen
*Assistant Examiner* — Marjan Fardanesh
(74) *Attorney, Agent, or Firm* — Global IP Counselors, LLP

(57) ABSTRACT

A light absorption coefficient distribution estimation device includes a detection section and a light absorption coefficient distribution estimation section. The detection section detects the received light intensity of scattered light from a subject at a plurality of light-receiving positions that differ in distance from an irradiation position at which measurement light is applied to the subject. The light absorption coefficient distribution estimation section estimates the light absorption coefficient distribution of the subject using the received light intensity, a propagation optical path length model that specifies a propagation optical path length on a basis of the distance, and a first model that specifies the received light intensity on a basis of the distance when absorption of light is at a predetermined value.

7 Claims, 9 Drawing Sheets

(56) References Cited

U.S. PATENT DOCUMENTS

2010/0256920 A1 10/2010 Amano et al.
2012/0010477 A1 1/2012 Amano et al.

FOREIGN PATENT DOCUMENTS

| JP | 2007-259967 A | 10/2007 |
|---|---|---|
| JP | 2008-049091 A | 3/2008 |
| JP | 2010-237139 A | 10/2010 |
| JP | 2012-019833 A | 2/2012 |

(1)

(2)

LIGHT ABSORPTION COEFFICIENT DISTRIBUTION ESTIMATION DEVICE, CONCENTRATION MEASUREMENT DEVICE, AND METHOD FOR CONTROLLING LIGHT ABSORPTION COEFFICIENT DISTRIBUTION ESTIMATION DEVICE

Japanese Patent Application No. 2012-153552 filed on Jul. 9, 2012, is hereby incorporated by reference in its entirety.

BACKGROUND

A concentration measurement method that measures the concentration of a specific component in a biological object (subject) has been developed. For example, a technique has been developed that measures the blood glucose level by collecting blood from a fingertip or the like, and measuring the enzymatic activity against glucose in blood.

However, the above blood glucose level measurement method is invasive, and is painful or unpleasant for the subject. Therefore, a technique that applies near-infrared light to the surface of a part (e.g., hand) of a human body, and measures the blood glucose level from the light absorption has been developed as a non-invasive blood glucose level measurement method.

For example, JP-A-2010-237139, JP-A-2007-259967, and JP-A-2008-49091 disclose a technique that calculates the concentration of glucose in the dermis by utilizing reflected light (scattered light) obtained by applying light to the biological object.

JP-A-2007-259967 and JP-A-2008-49091 disclose a probe that is brought into contact with the biological object, and includes a plurality of irradiation sections that apply measurement light to the biological object, and one light-receiving section that receives scattered light from the biological object. In JP-A-2007-259967 and JP-A-2008-49091, the irradiation section and the light-receiving section are disposed so that the ratio of scattered light from the dermis increases. More specifically, scattered light from the dermis is selectively received by setting the distance between the irradiation section and the light-receiving section to a specific value (i.e., 0.65 mm).

When using the above method, however, light received by the light-receiving section may include light that has propagated in a skin layer (e.g., epidermis or subcutis) other than the dermis. The dermis contains a plurality of components other than glucose. The glucose concentration may not be accurately determined when light that has propagated in a skin layer other than the dermis (i.e., error) is mixed into light received by the light-receiving section. The above problem also occurs when the measurement target component is not glucose.

SUMMARY

According to one aspect of the invention, there is provided light absorption coefficient distribution estimation device comprising:

a detection section that detects a received light intensity of scattered light from a subject at a plurality of light-receiving positions that differ in distance from an irradiation position at which measurement light is applied to the subject; and a light absorption coefficient distribution estimation section that estimates a light absorption coefficient distribution of the subject using the received light intensity, a propagation optical path length model that specifies a propagation optical path length on a basis of the distance, and a first model that specifies the received light intensity on a basis of the distance when absorption of light is at a predetermined value.

According to another aspect of the invention, there is provided control method comprising:

detecting a received light intensity of scattered light from a subject at a plurality of light-receiving positions that differ in distance from an irradiation position at which measurement light is applied to the subject; and estimating a light absorption coefficient distribution of the subject using the received light intensity, a propagation optical path length model that specifies a propagation optical path length on a basis of the distance, and a first model that specifies the received light intensity on a basis of the distance when absorption of light is at a predetermined value.

DESCRIPTION OF EXEMPLARY EMBODIMENTS

Figure 1:
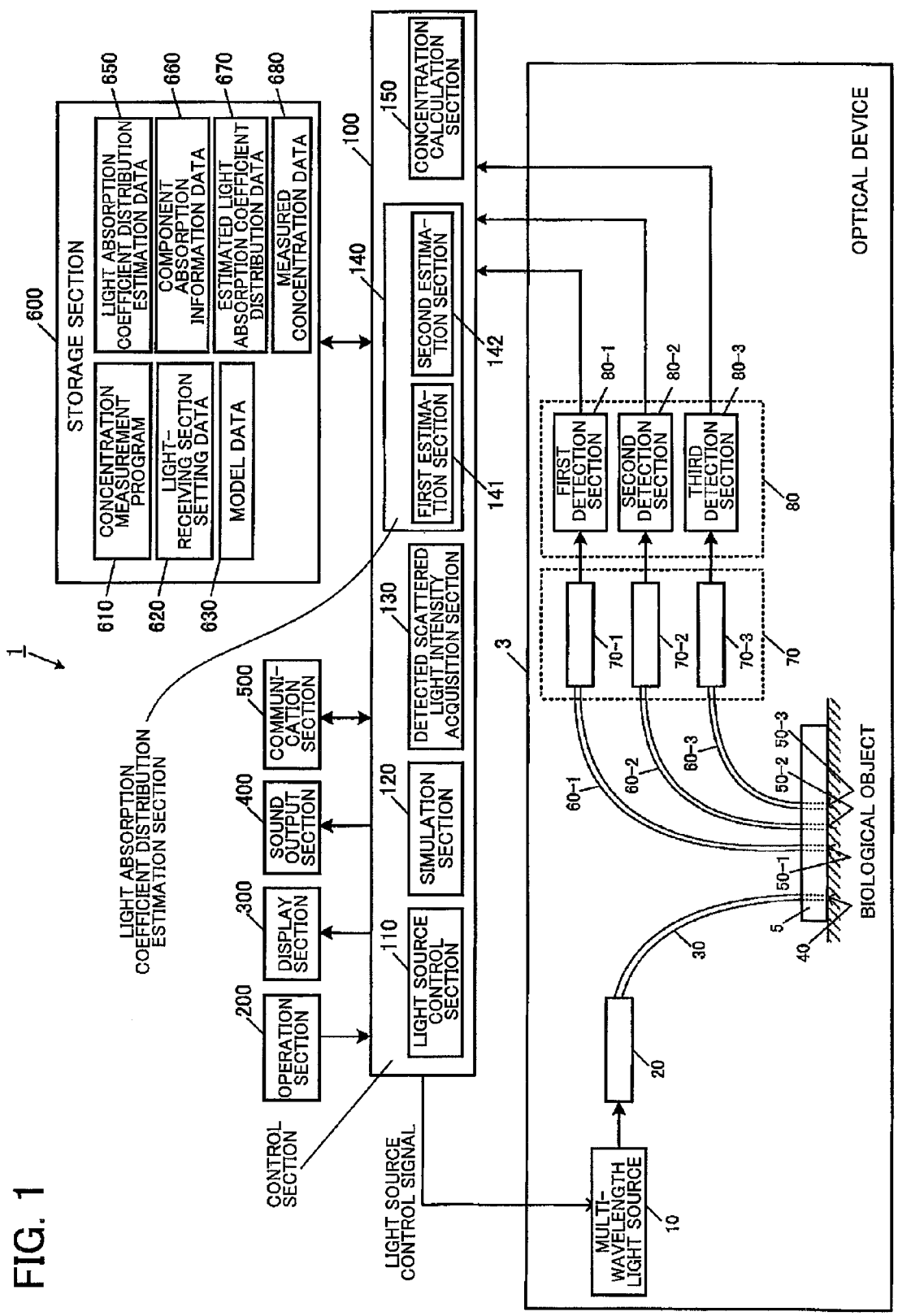
FIG. 1 is a block diagram illustrating an example of the functional configuration of a concentration measurement device.

Several embodiments of the invention may implement a novel technique for accurately estimating the light absorption coefficient distribution of the subject by utilizing the optical characteristics of a substance.

For example, when the subject has a plurality of layers (e.g., skin), the light absorption characteristics may differ between the layers. Therefore, the concentration of each component in a given part of the subject can be accurately measured by analyzing the difference in light absorption characteristics between the parts of the subject.

According to one embodiment of the invention, there is provided a light absorption coefficient distribution estimation device comprising:

a detection section that detects a received light intensity of scattered light from a subject at a plurality of light-receiving positions that differ in distance from an irradiation position at which measurement light is applied to the subject; and a light absorption coefficient distribution estimation section that estimates a light absorption coefficient distribution of the subject using the received light intensity, a propagation optical path length model that specifies a propagation optical path length on a basis of the distance, and a first model that specifies the received light intensity on a basis of the distance when absorption of light is at a predetermined value.

According to another embodiment of the invention, there is provided a control method comprising:

detecting a received light intensity of scattered light from a subject at a plurality of light-receiving positions that differ in distance from an irradiation position at which measurement light is applied to the subject; and estimating a light absorption coefficient distribution of the subject using the received light intensity, a propagation optical path length model that specifies a propagation optical path length on a basis of the distance, and a first model that specifies the received light intensity on a basis of the distance when absorption of light is at a predetermined value.

According to the above configuration, the received light intensity of scattered light from the subject is detected at a plurality of light-receiving positions that differ in distance from the irradiation position at which the measurement light is applied to the subject. Specifically, a plurality of light-receiving positions are provided in advance, and the received light intensity of scattered light is detected at the plurality of light-receiving positions. The light absorption coefficient distribution of the subject can be accurately estimated by utilizing the received light intensity of scattered light detected at the plurality of light-receiving positions, the propagation optical path length model that specifies the propagation optical path length on a basis of the distance from the irradiation position, and the zero-absorption scattered light intensity model. It is effective to apply the above method to a subject that has a plurality of layers (e.g., skin), for example. If the light absorption coefficient distribution of the subject can be accurately estimated, the concentration of a specific component in the subject can be accurately calculated by utilizing the light absorption coefficient.

In the light absorption coefficient distribution estimation device, the light absorption coefficient distribution estimation section may include a first estimation section that estimates the light absorption coefficient distribution using the received light intensity, the propagation optical path length, and the received light intensity when absorption of light is at the predetermined value, at an identical distance from the irradiation position.

According to the above configuration, the light absorption coefficient distribution of the subject can be estimated by utilizing the received light intensity, the propagation optical path length, and the received light intensity when absorption of light is zero, at an identical distance from the irradiation position.

In the light absorption coefficient distribution estimation device, the light absorption coefficient distribution estimation section may estimate the light absorption coefficient distribution additionally using a second model that specifies a degree of variation in propagation optical path length of a photon on a basis of the distance.

In the light absorption coefficient distribution estimation device, the light absorption coefficient distribution estimation section may include a second estimation section that estimates the light absorption coefficient distribution using the light absorption coefficient distribution estimated by the first estimation section and the degree of variation in the propagation optical path length at the identical distance.

According to the above configuration, the light absorption coefficient distribution is estimated using the propagation optical path length variation model that specifies the degree of variation in propagation optical path length of photons on a basis of the distance from the irradiation position in addition to the propagation optical path length model and the zero-absorption scattered light intensity model. The light absorption coefficient distribution can be more accurately estimated by utilizing the light absorption coefficient distribution estimated by the first estimation section and the degree of variation in the propagation optical path length at the identical distance.

In the light absorption coefficient distribution estimation device, the detection section may detect the received light intensity using a probe having a plurality of light-receiving sections that are provided circularly around an irradiation section that applies the measurement light.

According to the above configuration, the measurement light is applied to the subject in a state in which the probe is brought into contact with the subject. The probe has a plurality of light-receiving sections that are circularly provided around the measurement light irradiation section. Therefore, the detection section can detect the intensity of scattered light from the subject at a plurality of light-receiving positions that differ in distance from the irradiation position by utilizing the probe.

The light absorption coefficient distribution estimation device may further comprise:

a normalization section that normalizes intensity of light received by the plurality of light-receiving sections that are provided concentrically.

When a plurality of light-receiving sections are circularly provided around the irradiation section, the received light intensity of scattered light received by each light-receiving section may differ due to the difference in light-receiving area, for example. A received light intensity that is appropriate for the calculation of the light absorption coefficient distribution can be determined by normalizing the intensity of light received by the light-receiving sections that are provided concentrically.

In the light absorption coefficient distribution estimation device, the detection section may detect the received light intensity using a probe having a light-receiving section that is formed by a line sensor or an area sensor.

According to the above configuration, the received light intensity of scattered light can be effectively detected by utilizing the probe that is brought into contact with the subject, and provided with the light-receiving section that is formed by a line sensor or an area sensor.

According to another embodiment of the invention, there is provided a concentration measurement device comprising:

the light absorption coefficient distribution estimation device; and a concentration calculation section that calculates a concentration of a specific component in the subject using the light absorption coefficient distribution estimated by the light absorption coefficient distribution estimation section.

According to the above configuration, the concentration of a specific component in the subject can be calculated by utilizing the light absorption coefficient distribution estimated by the light absorption coefficient distribution estimation device.

Exemplary embodiments of the invention are described below with reference to the drawings. In the exemplary embodiments, measurement light is applied to the subject (biological object) (i.e., skin), and the light absorption coefficient distribution of skin is estimated based on scattered light from the skin. The concentration of glucose in the dermis of the skin is measured using the estimated light absorption coefficient. Note that the invention is not limited to the following exemplary embodiments.

Human skin is roughly classified into the epidermis, the dermis, and the subcutis. Among these, the dermis has developed capillaries, and the concentration of glucose in the dermis changes corresponding to the concentration of glucose in blood. The following exemplary embodiments aim at estimating the blood glucose level in the subject by measuring the concentration of glucose in the dermis.

1. Configuration

FIG. 1 is a block diagram illustrating an example of a functional configuration of a concentration measurement device 1 according to one embodiment of the invention. The concentration measurement device 1 includes a light absorption coefficient distribution estimation device that estimates the light absorption coefficient distribution in skin, and measures the concentration of glucose in the dermis of skin using the light absorption coefficient distribution in skin estimated by the light absorption coefficient distribution estimation device. Note that the following embodiments are described and illustrated on the assumption that the light absorption coefficient distribution estimation device and the concentration measurement device are integrated in a single device.

The concentration measurement device 1 includes an optical device 3, a control section 100, an operation section 200, a display section 300, a sound output section 400, a communication section 500, and a storage section 600 as the main elements.

The optical device 3 includes a probe 5, a multi-wavelength light source 10, a measurement light incident section 20, a measurement light guide section 30, an irradiation section 40, three light-receiving sections 50 (50-1, 50-2, 50-3), three scattered light guide sections 60 (60-1, 60-2, 60-3), three scattered light emission sections 70 (70-1, 70-2, 70-3), and three detection sections 80 (80-1, 80-2, 80-3). The light-receiving section 50, the scattered light guide section 60, the scattered light emission section 70, and the detection section 80 are provided on a one-to-one basis.

The probe 5 applies measurement light to a biological object, and receives scattered light from the biological object in a state in which the probe 5 comes in contact with the surface of the biological object. The probe 5 may be configured as a circular or rectangular patch-type probe, for example.

The multi-wavelength light source 10 is a light source that is configured to generate and output a plurality of lights that differ in wavelength. For example, the multi-wavelength light source 10 includes a multi-wavelength semiconductor laser. The multi-wavelength light source 10 generates light having a designated wavelength based on a light source control signal output from the control section 100, and emits the generated light as the measurement light. The measurement light may be pulsed light, or may be continuous light.

The measurement light incident section 20 is a light incident element that receives the measurement light output from the multi-wavelength light source 10. The measurement light incident section 20 is connected to the measurement light guide section 30, and guides the measurement light incident from the multi-wavelength light source 10 to the measurement light guide section 30.

The measurement light guide section 30 is a light guide that guides the measurement light incident from the measurement light incident section 20 to the irradiation section 40. For example, the measurement light guide section 30 includes an optical fiber. One end of the measurement light guide section 30 is connected to the measurement light incident section 20, and the other end of the measurement light guide section 30 is connected to the irradiation section 40 of the probe 5.

The irradiation section 40 is a light irradiator that applies the measurement light guided by the measurement light guide section 30 to the biological object. For example, the irradiation section 40 includes a lens or the like.

The light-receiving section 50 is a photoreceiver that is provided at a plurality of light-receiving positions that differ in distance from the measurement light irradiation position of the irradiation section 40, and receives scattered light from the biological object. For example, the light-receiving section 50 includes a lens or the like.

The scattered light guide section 60 is a light guide that guides the scattered light received by the light-receiving section 50 to the scattered light emission section 70. For example, the scattered light guide section 60 includes an optical fiber. One end of the scattered light guide section 60 is connected to the scattered light emission section 70, and the other end of the scattered light guide section 60 is connected to the light-receiving section 50.

The scattered light emission section 70 guides the scattered light guided by the scattered light guide section 60 to the corresponding detection section 80.

The detection section 80 detects the intensity of the scattered light emitted from the scattered light emission section 70. The detection section 80 includes a photodetector (e.g., phototube, photomultiplier, or photodiode), for example. The detection section 80 outputs a light detection signal including the detected light intensity to the control section 100.

The control section 100 is a control device/calculation device that controls each section of the concentration measurement device 1 and the optical device 3 according to a program (e.g., system program) stored in the storage section 600. The control section 100 includes a processor (e.g., central processing unit (CPU) or digital signal processor (DSP)) for example.

The control section 100 includes a light source control section 110, a simulation section 120, a detected scattered light intensity acquisition section 130, a light absorption coefficient distribution estimation section 140, and a concentration calculation section 150 as the main functional sections. Note that these functional sections are merely examples, and the control section 100 need not necessarily include all of these functional sections. A functional section other than these functional sections may be added as an essential element.

The light source control section 110 controls the light generation/output process performed by the multi-wavelength light source 10. More specifically, the light source control section 110 outputs the light source control signal that indicates the wavelength of light and instructs to generate light to the multi-wavelength light source 10 so that the multi-wavelength light source 10 generates and outputs a plurality of lights that differ in wavelength.

The simulation section 120 performs a given simulation process before concentration measurement to calculate a layer-basis propagation optical path length model that specifies the propagation optical path length of each skin layer corresponding to the distance from the measurement light irradiation position, a zero-absorption scattered light intensity model that specifies the received light intensity corresponding to the distance from the measurement light irradiation position when absorption of light is zero, and a layer-basis photon propagation optical path length variation model that specifies the degree of variation in each photon propagation optical path length. The simulation section 120 stores the calculated models in the storage section 600 as model data 630.

The simulation process performed by the simulation section 120 is described below.

The simulation section 120 performs the simulation process to calculate the propagation optical path length of each skin layer when applying measurement light having each candidate wavelength to a given skin model (hereinafter referred to as "layer-basis propagation optical path length"), the scattered light intensity when absorption of light by skin is zero (zero-absorption) (hereinafter referred to as "zero-absorption scattered light intensity"), and the degree of variation in layer-basis propagation optical path length for each photon (hereinafter referred to as "photon propagation optical path length variation"). In this case, the simulation section 120 calculates the moving distance of a plurality of (e.g., $10^8$) photons. The number of photons incident on the skin model is referred to as an incident photon count "$N_{in}$".

The candidate wavelength is a wavelength that is determined to be a candidate for the wavelength of the measurement light used to calculate the concentration of glucose in the dermis. It is effective to select a wavelength that can separate the main components of skin as the candidate wavelength. More specifically, it is effective to select a wavelength that ensures that the light absorption coefficient of each main component becomes a maximum in the absorption spectrum of each main component (i.e., water, proteins, lipids, and glucose) of the dermis of skin as the candidate wavelength.

For example, the light absorption coefficient of glucose becomes a maximum when the wavelength is 1600 nm, and the light absorption coefficient of water becomes a maximum when the wavelength is 1450 nm. Therefore, a plurality of candidate wavelengths (631) may be selected to include 1450 nm and 1600 nm.

A simulation process that utilizes the Monte Carlo method (Monte Carlo simulation process) may be employed as the simulation process performed by the simulation section 120. The Monte Carlo simulation process first generates a skin model. The skin model is generated by determining the light scattering coefficient and the thickness of each skin layer. Since the light scattering coefficient and the thickness of each skin layer differ between individuals to only a small extent, it is effective to determine the light scattering coefficient and the thickness of each skin layer by collecting a sample in advance, for example. The thickness of the epidermis is about 0.3 mm, the thickness of the dermis is about 1.2 mm, and the thickness of the subcutis is about 3.0 mm.

The parameters of the skin model may be determined by a method other than the above method. For example, the light scattering coefficient and the thickness of each skin layer may be measured each time the concentration is measured to determine the parameters of the skin model.

The light absorption coefficient distribution of skin is estimated using the zero-absorption scattered light intensity. Therefore, the Monte Carlo simulation process is performed on the assumption that the light absorption coefficient of the skin model is zero. More specifically, the simulation process is performed on the assumption that absorption of light is zero (zero-absorption).

When the simulation section 120 has generated the skin model, the simulation section 120 performs the simulation process that applies the measurement light having the candidate wavelength to the skin model. More specifically, the simulation section 120 performs a calculation process that applies a photon (luminous flux) (applied light model) to the skin model. The photon that has been applied to the skin model moves inside the skin model. The distance dl and the direction θ when the photon travels to the next point are determined using a random number.

The simulation section 120 calculates the distance dl when the photon travels to the next point using the following expression (1).

$$dl = -\ln(R)/\mu_{sm} \quad (1)$$

where, ln(A) is a natural logarithm of A, $\mu_{sm}$ is the light scattering coefficient of the mth layer (epidermis, dermis, or subcutis) of the skin model, and R is a random number from 0 to 1. The expression (1) is based on the assumption that absorption of light does not occur (i.e., light absorption coefficient is zero) when the photon travels inside the skin model.

The simulation section 120 calculates the direction θ when the photon travels to the next point using the following expression (2).

$$\cos\theta = \begin{cases} \frac{1}{2g}\left\{1 + g^2 - \left[\frac{1-g^2}{1-g+2g\xi}\right]^2\right\} & \text{if } g \neq 0 \\ 2\xi - 1 & \text{if } g = 0 \end{cases} \quad (2)$$

where, g is the anisotropy parameter that is the average value of the cosine of the scattering angle (the anisotropy parameter of skin is about 0.9), and ξ is a random number from 0 to 1.

The simulation section 120 repeats the calculations using the expressions (1) and (2) every unit time to calculate the moving path of the photon from the measurement light irradiation position to the position of the light-receiving section. Since the three light-receiving sections 50 are provided, the simulation section 120 calculates the moving path of the photon from the measurement light irradiation position to the position of each light-receiving section 50. The distance from the irradiation position to the position of the light-receiving section is referred to as "light-receiving section distance R".

The moving path of each photon that has reached the position away from the irradiation position by each light-receiving section distance R is classified on a layer basis (i.e., on a basis of the layers through which the moving path passes). The total optical path length of the moving path of the photon that has reached the position away from the irradiation position by each light-receiving section distance R is calculated every unit time on a layer basis to acquire the layer-basis propagation optical path length.

The simulation section 120 performs the simulation process to calculate the scattered light intensity when the light absorption coefficient is zero and the incident photon count is $N_{in}$. More specifically, the simulation section 120 performs the simulation process to calculate the intensity of scattered light received at the position away from the irradiation position by each light-receiving section distance R.

The simulation section 120 calculates the degree of variation in propagation optical path length of each photon that has propagated in each skin layer. The degree of variation in propagation optical path length of each photon that has propagated in each skin layer is calculated by calculating the difference between the average value of the propagation distance of each photon (received at the above position) in each layer and the propagation distance of one photon (received at the above position) in each layer.

More specifically, the moving distance $l_{km}$ of each photon in each skin layer is calculated by the Monte Carlo simulation process, and stored. Note that the suffix "k" is the number of the photon, and the suffix "m" is the number of the skin layer.

Specifically, the moving distance $l_{km}$ refers to the moving distance of the kth photon in the mth skin layer. In this case, the degree of variation $\delta_{km}(r)$ in propagation optical path length of the photon received at the position away from the irradiation position by a distance r is calculated by the following expressions (3) and (4).

$$\delta_{km}(r) = l_{km}(r) - L'_m(r) \tag{3}$$

$$L'_m(r) = \frac{L_m(r)}{N(r)} \tag{4}$$

The actual simulation results are shown below in order to explain the results obtained by the Monte Carlo simulation process. The distance the incident position (at which the measurement light is incident on the biological object) to the emission position (at which scattered light is emitted) is referred to as "incidence-to-emission distance r". The incidence-to-emission distance r is a parameter that differs from the light-receiving section distance R, and is introduced for explaining the principle. Discrete values at constant intervals were set as the incidence-to-emission distance r, and the simulation process was performed using a plurality of incidence-to-emission distances r.

Figure 3:
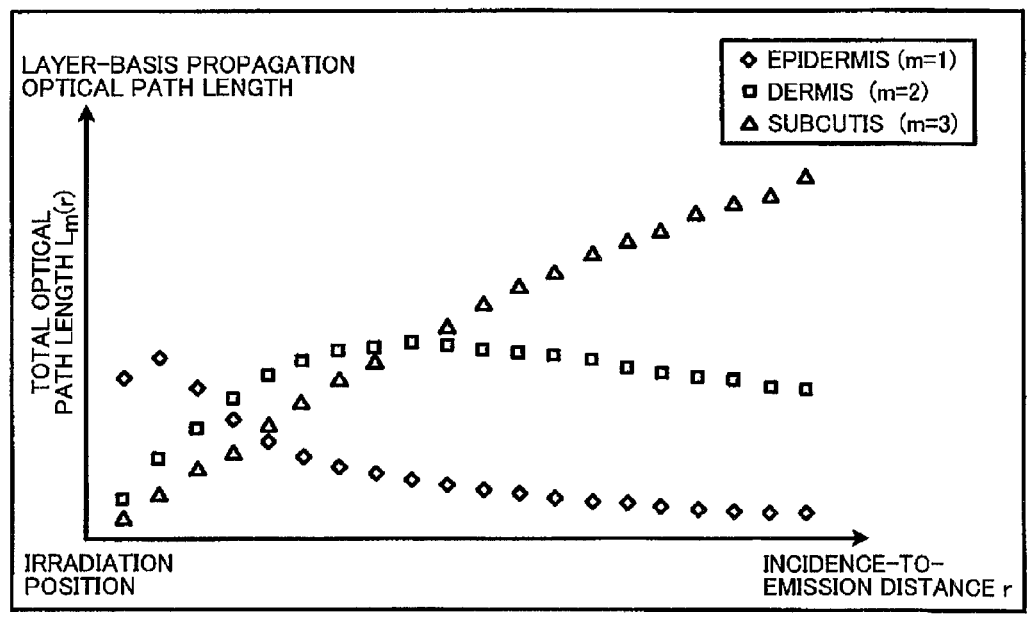
FIG. 3(1) is a view illustrating an example of a propagation optical path length distribution, and FIG. 3(2) is a view illustrating an example of a zero-absorption scattered light intensity space-resolved waveform.
Figure 3:
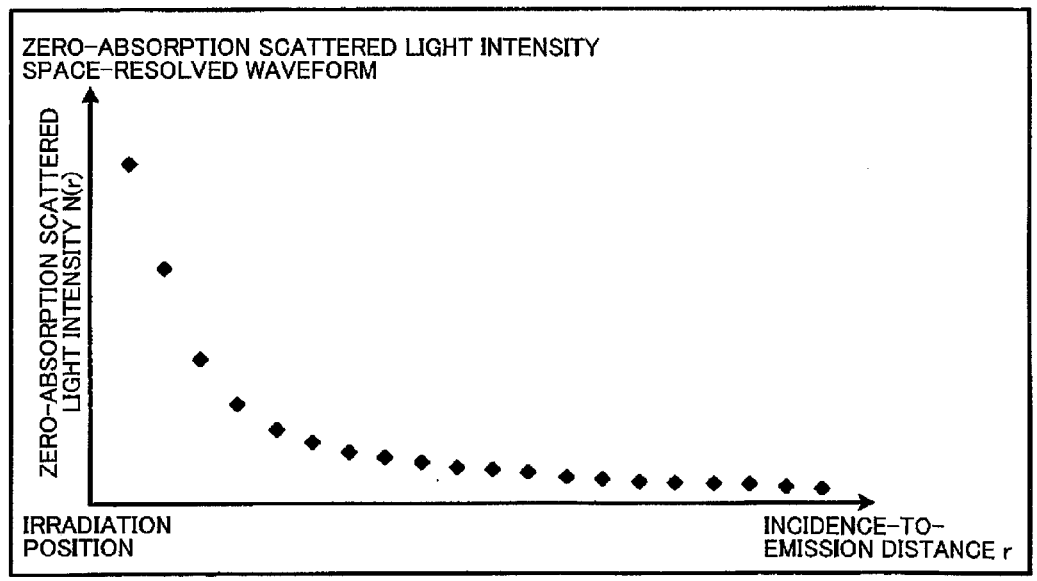

FIG. 3(1) is a view illustrating an example of the results for the layer-basis propagation optical path length that was calculated by the simulation process using one candidate wavelength. The layer-basis propagation optical path length shows the distribution of the propagation optical path length in skin (i.e., propagation optical path length distribution). In FIG. 3(1), the horizontal axis indicates the incidence-to-emission distance r, and the vertical axis indicates the total optical path length $L_m(r)$. Note that the suffix "m" is the number of the skin layer. The number of the epidermis is "1" (m=1), the number of the dermis is "2" (m=2), and the number of the subcutis is "3" (m=3).

In FIG. 3(1), the total optical path length of the epidermis is indicated by a white diamond, the total optical path length of the dermis is indicated by a white square, and the total optical path length of the subcutis is indicated by a white triangle. As illustrated in FIG. 3(1), the total optical path length $L_m(r)$ tends to become a maximum at a position near the irradiation position as the distance from the skin surface decreases.

FIG. 3(2) is a view illustrating an example of the results for the scattered light intensity when the light absorption coefficient is zero and the incident photon count is $N_{in}$ that was calculated by the simulation process using one candidate wavelength. In FIG. 3(2), the horizontal axis indicates the incidence-to-emission distance r, and the vertical axis indicates the zero-absorption scattered light intensity N(r). The waveform of the zero-absorption scattered light intensity is the spatially-resolved waveform of the scattered light intensity when absorption of light by skin is zero (i.e., zero-absorption scattered light intensity spatially-resolved waveform).

As illustrated in FIG. 3(2), the zero-absorption scattered light intensity N(r) tends to attenuate as the incidence-to-emission distance r increases. This means that the number of photons that reach the target position decreases as the distance from the irradiation position increases. Note that the zero-absorption scattered light intensity N(r) (vertical axis) is synonymous with the number of photons received at the same position.

Again referring to FIG. 1, the detected scattered light intensity acquisition section 130 acquires the intensity of scattered light (hereinafter referred to as "detected scattered light intensity") detected by each of the three detection sections 80. The detected scattered light intensity is synonymous with the intensity (received light intensity) of light received by the light-receiving section 50.

Figure 4:
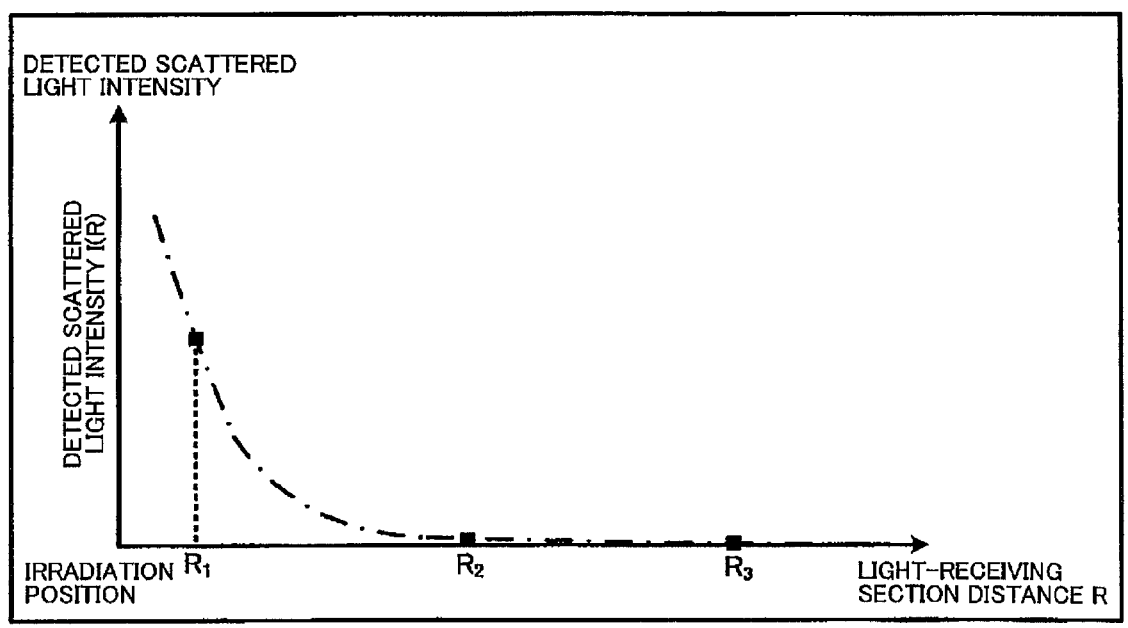
FIG. 4 a view illustrating an example of a detected scattered light intensity waveform.

FIG. 4 is a view illustrating an example of the results for the detected scattered light intensity detected by the detection section 80 at a given wavelength. In FIG. 4, the horizontal axis indicates the light-receiving section distance R, and the vertical axis indicates the detected scattered light intensity I(R). The scattered light intensities detected by the three detection sections 80 (80-1, 80-2, 80-3) are indicated by a black square, and a curve obtained by function fitting is indicated by a dash-dotted line. As illustrated in FIG. 4, the detected scattered light intensity I(R) tends to attenuate as the light-receiving section distance R increases. This means that the number of photons received decreases as the distance from the irradiation position increases.

The light absorption coefficient distribution estimation section 140 estimates the light absorption coefficient distribution (i.e., the distribution of the light absorption coefficient of skin). The light absorption coefficient distribution estimation section 140 includes a first estimation section 141 (functional section) that estimates the light absorption coefficient distribution using the received light intensity, the propagation optical path length, and the received light intensity when absorption of light is zero, at an identical distance from the irradiation position. The light absorption coefficient distribution estimation section 140 also includes a second estimation section 142 (functional section) that estimates the light absorption coefficient distribution additionally using the propagation optical path length variation model that specifies the degree of variation in propagation optical path length of photons on a distance basis.

The light absorption coefficient distribution estimation section 140 estimates the light absorption coefficient distribution of the subject using the model parameter values acquired by the simulation section 120 as a result of the simulation process, and the detected scattered light intensity acquired by the detected scattered light intensity acquisition section 130. When the subject is skin, the light absorption coefficient of each skin layer (hereinafter referred to as "layer-basis light absorption coefficient") is estimated as the light absorption coefficient distribution.

The model parameter values and the detected scattered light intensities in a number equal to or larger than the number of skin layers are required to estimate the layer-basis light absorption coefficient (the details thereof are described later). Since the number of skin layers is three, three or more pieces of data are required to estimate the layer-basis light absorption coefficient. Therefore, three light-receiving section 50 and three detection sections 80 are provided, and the light absorption coefficient distribution is estimated using three model parameter values acquired by the simulation section 120 as a result of the simulation process, and three detected scattered light intensities acquired from the three detection sections 80.

The concentration calculation section 150 calculates the concentration of glucose in the dermis of skin using the light absorption coefficient distribution estimated by the light absorption coefficient distribution estimation section 140.

The light absorption coefficients of the dermis in a number equal to or larger than the number of main components of skin are required to calculate the concentration of glucose in the dermis. Water, proteins, glucose, and lipids may be considered to be the main components of skin. In this case, four light absorption coefficients of the dermis are required to calculate the concentration of glucose in the dermis. Therefore, four wavelengths are selected from the candidate wavelengths (631), and the layer-basis light absorption coefficient is estimated for each selected wavelength. The concentration of glucose in the dermis is calculated using the light absorption coefficient of the dermis corresponding to each wavelength.

The operation section 200 is an input device that includes a button switch and the like. The operation section 200 outputs a signal to the control section 100 when a button has been pressed. The user inputs data or instructions (e.g., glucose concentration measurement start instruction) by operating the operation section 200.

The display section 300 is a display that displays an image based on a display signal output from the control section 100. The display section 300 includes a liquid crystal display (LCD) or the like. The display section 300 displays information about the concentration of glucose calculated by the concentration calculation section 150, for example.

The sound output section 400 is a sound output device that outputs a sound based on a sound output signal output from the control section 100. The sound output section 400 includes a speaker or the like. The sound output section 400 outputs a glucose concentration measurement guidance sound, an alarm sound, and the like.

The communication section 500 is a communication device that exchanges information used in the device with an external information processing device under control of the control section 100. The communication section 500 may utilize a cable communication method via a cable conforming to a given communication standard, a communication method via an intermediate device (cradle) that also serves as a charger, a wireless communication method that utilizes short-range wireless communication, or the like.

The storage section 600 includes a memory (e.g., read-only memory (ROM), flash ROM, and random access memory (RAM)). The storage section 600 stores a system program for the control section 100, a program that implements various functions (e.g., concentration measurement function), data, and the like. The storage section 600 includes a work area that temporarily stores processing target data, processing results, and the like.

Figure 7:
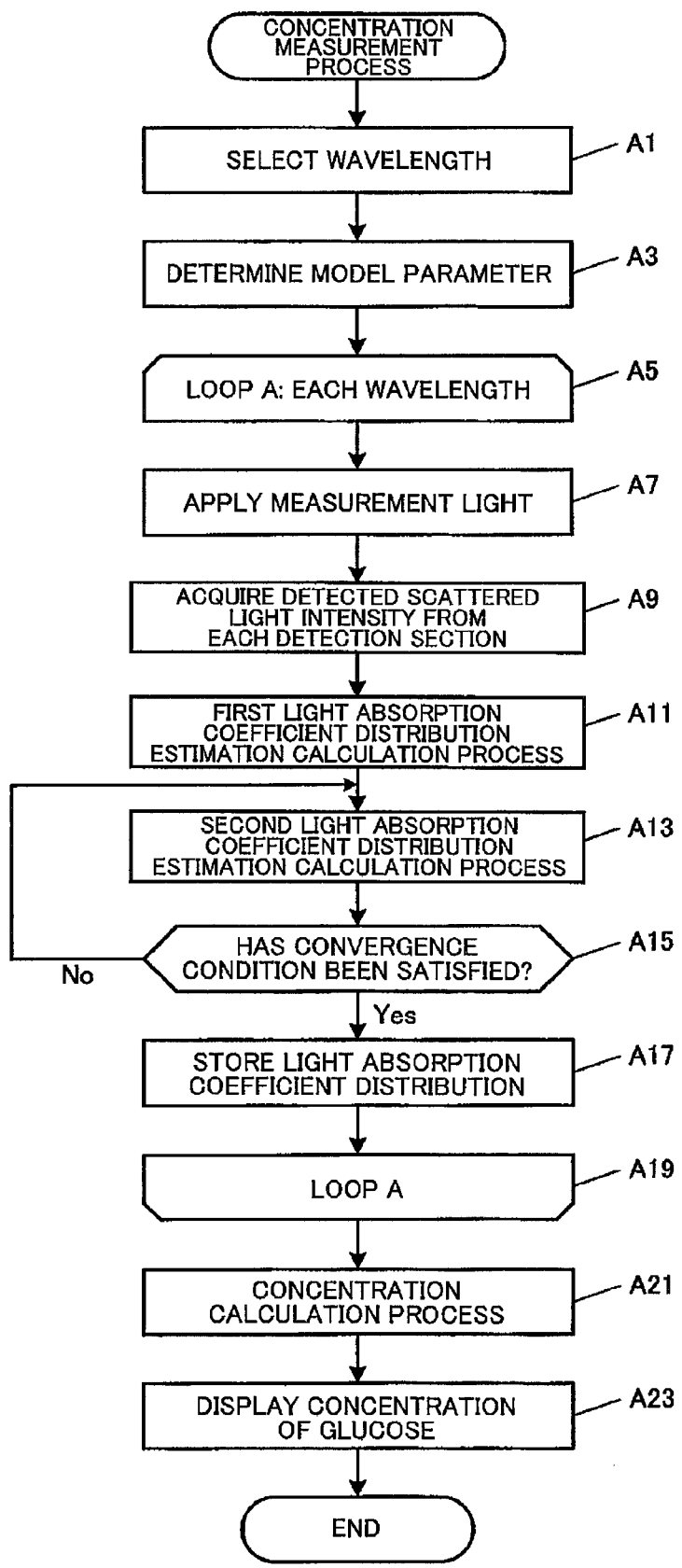
FIG. 7 is a flowchart illustrating the flow of a concentration measurement process.

The storage section 600 stores a concentration measurement program 610 that is read by the control section 100, and implements a concentration measurement process (see FIG. 7). The details of the concentration measurement process are described later using a flowchart.

The storage section 600 stores light-receiving section setting data 620, model data 630, light absorption coefficient distribution estimation data 650, component absorption information data 660, estimated light absorption coefficient distribution data 670, and measured concentration data 680, for example.

Figure 2:
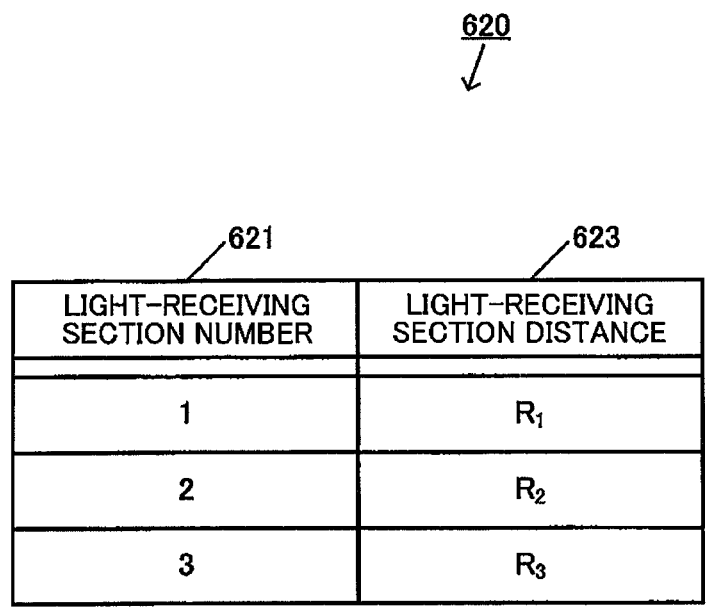
FIG. 2 is a view illustrating an example of the data configuration of light-receiving section setting data.

The light-receiving section setting data 620 is setting data pertaining to the arrangement of the light-receiving section 50. FIG. 2 illustrates a data configuration example of the light-receiving section setting data 620. The light-receiving section setting data 620 includes a light-receiving section number 621 that indicates the number of the light-receiving section 50, and a light-receiving section distance 623 that indicates the distance from the irradiation position to the position of the light-receiving section 50. Since the three light-receiving sections 50 are provided, the light-receiving section distance $R_n$ (=$R_1$ to $R_3$) is specified for each light-receiving section 50. Note that the suffix "n" (=1 to 3) is the number of the light-receiving section 50.

Figure 5:
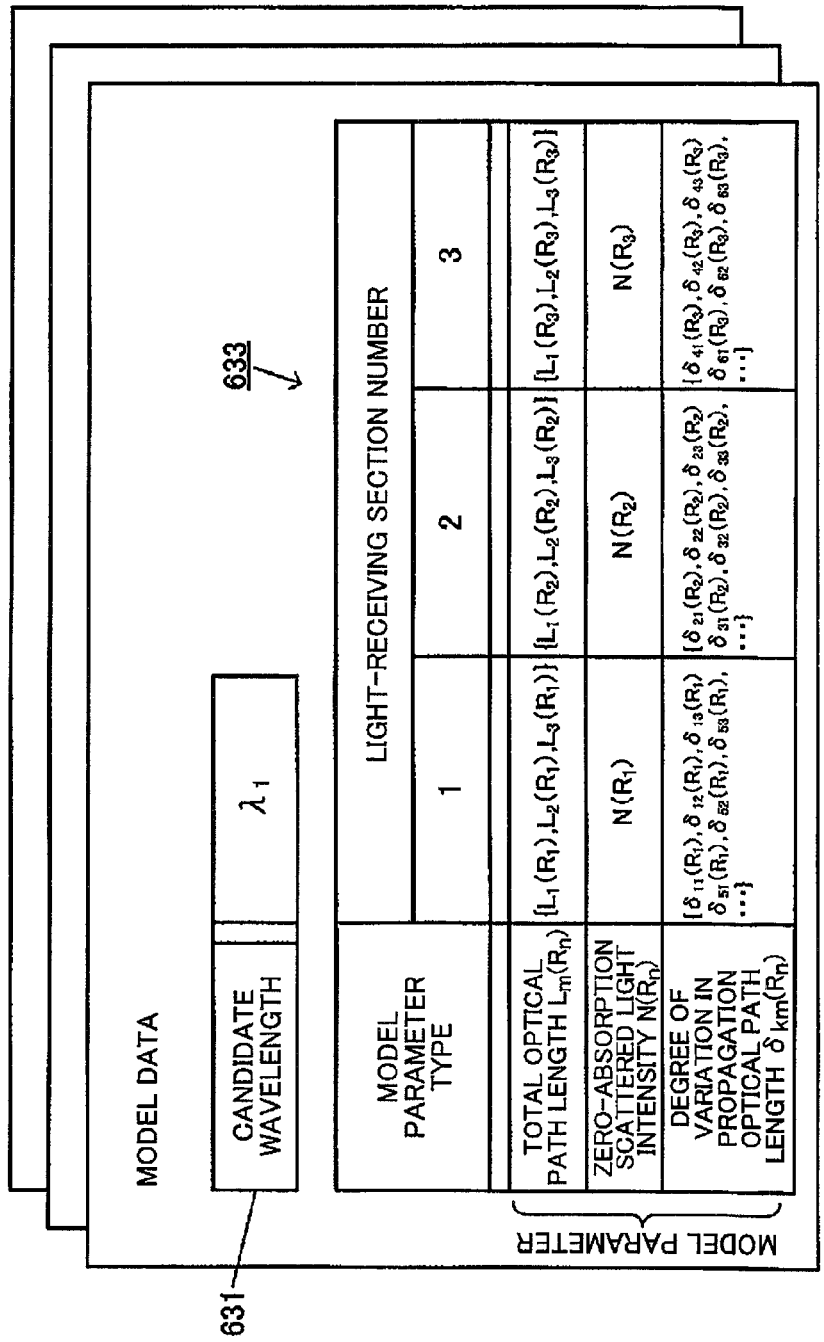
FIG. 5 is a view illustrating an example of the data configuration of model data.

The model data 630 is data pertaining to the model acquired by the simulation section 120 as a result of the simulation process. FIG. 5 illustrates a data configuration example of the model data 630. The model data 630 includes a candidate wavelength 631 and a model parameter table 633. Since the simulation section 120 performs the simulation process using a plurality of candidate wavelengths (631), the model data is stored corresponding to the plurality of candidate wavelengths (631).

The model parameter table 633 stores a model parameter type and a light-receiving section number. The light-receiving section number is the same as the light-receiving section number 621 illustrated in FIG. 2. The model parameter type includes the total optical path length $L_m(R_n)$, the zero-absorption scattered light intensity $N(R_n)$, and the degree of variation $\delta_{km}(R_n)$ in propagation optical path length at the light-receiving section distance $R_n$ corresponding to the light-receiving section 50 having the corresponding light-receiving section number. These parameters are referred to as "model parameter".

For example, the light-receiving section distance of the light-receiving section 50 having the light-receiving section number 1 is $R_1$. Therefore, $\{L_1(R_1), L_2(R_1), L_3(R_1)\}$ is stored as the total optical path length of each skin layer, and $N(R_1)$ is stored as the zero-absorption scattered light intensity. In the data example illustrated in FIG. 5, $\{\delta_{11}(R_1), \delta_{12}(R_1), \delta_{13}(R_1), \delta_{51}(R_1), \delta_{52}(R_1), \delta_{53}(R_1), \ldots\}$ is stored as the degree of variation in propagation optical path length (i.e., the first photon, the fifth photon, . . . have been received by the light-receiving section 50 having the light-receiving section number 1). The above description similarly applies to the light-receiving section 50 having the light-receiving section number 2 and the light-receiving section 50 having the light-receiving section number 3.

Figure 6:
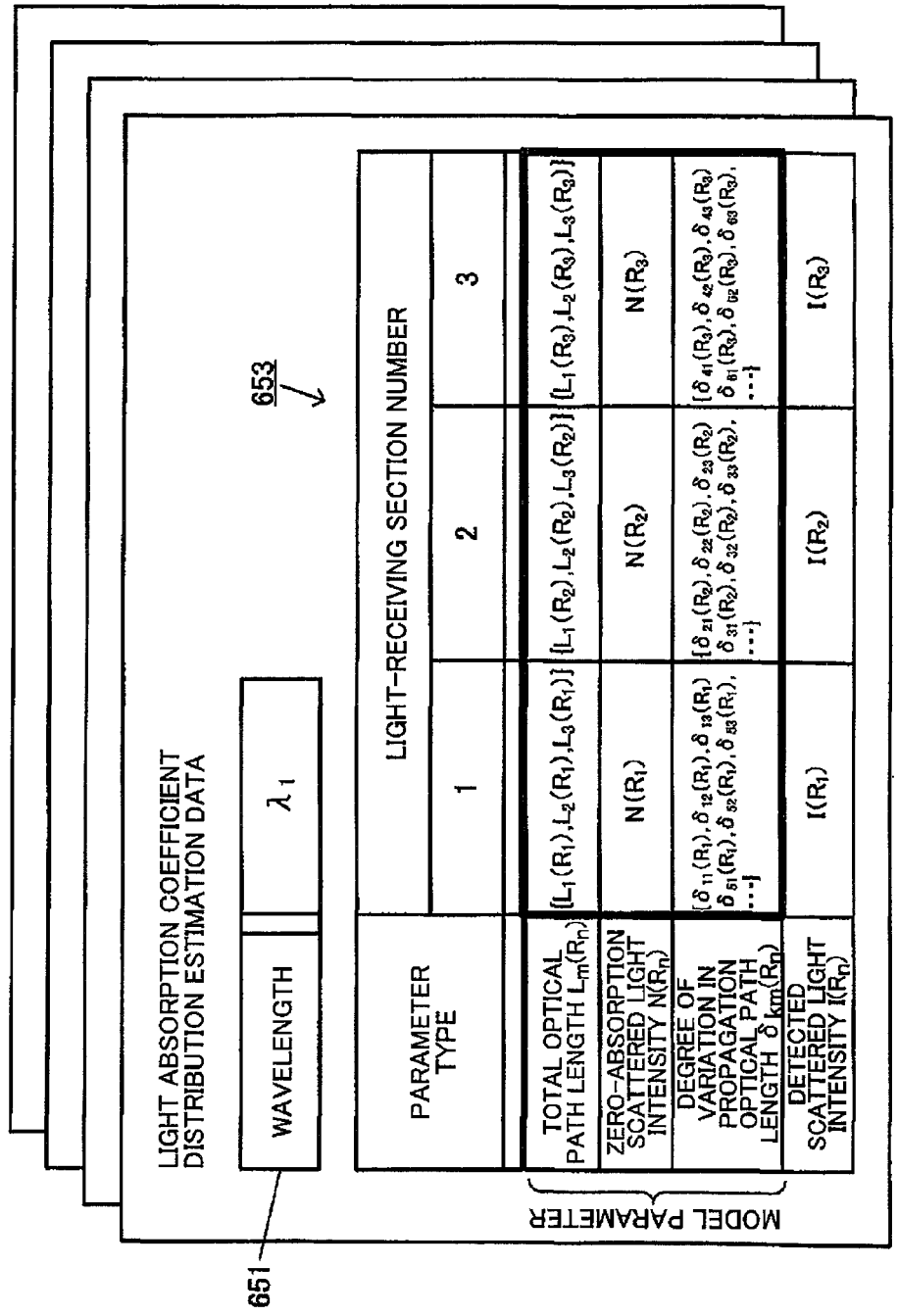
FIG. 6 is a view illustrating an example of the data configuration of light absorption coefficient distribution estimation data.

The light absorption coefficient distribution estimation data 650 is data that is used by the light absorption coefficient distribution estimation section 140 to estimate the light absorption coefficient distribution. FIG. 6 illustrates a data configuration example of the light absorption coefficient distribution estimation data 650. The light absorption coefficient distribution estimation data 650 includes a wavelength 651 and a parameter table 653.

The wavelength 651 indicates four wavelengths selected from the plurality of candidate wavelengths (631). The parameter table 653 is a table that stores parameters required to estimate the light absorption coefficient distribution. The parameter table 653 stores a parameter type and a light-receiving section number.

The parameter type includes the total optical path length $L_m(R_n)$ at the light-receiving section distance $R_n$ corresponding to the light-receiving section 50 having the corresponding light-receiving section number, the zero-absorption scattered light intensity $N(R_n)$, the degree of variation $\delta_{km}(R_n)$ in propagation optical path length, and the detected scattered light intensity $I(R_n)$. The total optical path length $L_m(R_n)$, the zero-absorption scattered light intensity $N(R_n)$, and the degree of variation $\delta_{km}(R_n)$ in propagation optical path length are model parameters acquired from the model data 630.

The component absorption information data 660 is data that indicates absorption information about the components contained in the dermis of skin. For example, the component absorption information data 660 includes the light absorption coefficient and the molar extinction coefficient of water, proteins, lipids, and glucose as the absorption information. The absorption information must be measured in advance, and stored in the storage section 600. The component absorption information data 660 is used to calculate the concentration of glucose in the dermis of skin.

The estimated light absorption coefficient distribution data 670 is data that indicates the light absorption coefficient distribution estimated by the light absorption coefficient distribution estimation section 140. The estimated light absorption coefficient distribution data 670 includes the estimated value of the layer-basis light absorption coefficient (i.e., the light absorption coefficient of each of the epidermis, the dermis, and the subcutis of skin). These values are calculated by solving given simultaneous equations when calculating the concentration of each component of the dermis. The details of the layer-basis light absorption coefficient calculation method are described later.

The measured concentration data 680 is data that indicates the calculation results for the concentration of a specific biological component that has been calculated by the concentration calculation section 150. For example, the measured concentration data 680 includes the concentration of glucose in the dermis of skin.

2. Flow of Process

FIG. 7 is a flowchart illustrating the flow of the concentration measurement process performed by the control section 100 according to the concentration measurement program 610 stored in the storage section 600.

In a step A1, the control section 100 selects wavelengths in the same number as the number of main components of skin from a plurality of candidate wavelengths (631). When water, proteins, glucose, and lipids are considered to be the main components of skin, the control section 100 selects four wavelengths from a plurality of candidate wavelengths.

The control section 100 then determines the model parameters for each wavelength selected in the step A1 (step A3). More specifically, the control section 100 reads the total optical path length $L_m(R_n)$, the zero-absorption scattered light intensity $N(R_n)$, and the degree of variation $\delta_{km}(R_n)$ in propagation optical path length at each light-receiving section distance $R_n$ referring to the model parameter table 633 of the candidate wavelength 631 that is included in the model data 630 and corresponds to each selected wavelength. The control section 100 stores the model parameters in the parameter table 653, generates the light absorption coefficient distribution estimation data 650 that is linked to the wavelength 651, and stores the generated light absorption coefficient distribution estimation data 650 in the storage section 600.

The control section 100 then performs a loop A process on each selected wavelength (steps A5 to A19). In the loop A process, the light source control section 110 causes the multi-wavelength light source 10 to generate light having each wavelength, and apply the generated light to the biological object as the measurement light (step A7).

The control section 100 then acquires the detected scattered light intensity $I(R_n)$ from each detection section 80 (step A9). The control section 100 stores the acquired detected scattered light intensity $I(R_n)$ in the parameter table 653 included in the light absorption coefficient distribution estimation data 650.

The first estimation section 141 included in the light absorption coefficient distribution estimation section 140 performs a first estimation calculation process that estimates the light absorption coefficient distribution according to the following expression (6) that is obtained by applying the following basic expression (5) to the three-layer structure of skin (step A11).

$$N(r)\ln\left(\frac{N'(r)}{I'(r)}\right) = \sum_{m=1}^{M} \mu_{am} L_m(r) \quad (5)$$

where, $N'(r) = \frac{N(r)}{N_{in}}, I'(r) = \frac{I(r)}{I_{in}}$ $$\begin{cases} N(R_1)\ln\left(\frac{N'(R_1)}{I'(R_1)}\right) = \mu_{a1}L_1(R_1) + \mu_{a2}L_2(R_1) + \mu_{a3}L_3(R_1) \\ N(R_2)\ln\left(\frac{N'(R_2)}{I'(R_2)}\right) = \mu_{a1}L_1(R_2) + \mu_{a2}L_2(R_2) + \mu_{a3}L_3(R_2) \\ N(R_3)\ln\left(\frac{N'(R_3)}{I'(R_3)}\right) = \mu_{a1}L_1(R_3) + \mu_{a2}L_2(R_3) + \mu_{a3}L_3(R_3) \end{cases} \quad (6)$$

The second estimation section 142 included in the light absorption coefficient distribution estimation section 140 performs a second estimation calculation process that estimates the light absorption coefficient distribution according to the following expression (8) that is obtained by applying the following basic expression (7) to the three-layer structure of skin (step A13).

$$N(r)\cdot\ln\left[\frac{I_{in}}{N_{in}}\cdot\frac{1}{I(r)}\sum_{k=1}^{N(r)}\exp\left(-\sum_{m=1}^{M}\mu_{am}\delta_{km}(r)\right)\right] = \sum_{m=1}^{M}\mu_{am}L_m(r) \quad (7)$$

$$\begin{cases} N(R_1)\ln\left[\frac{I_{in}}{N_{in}}\frac{1}{I(R_1)}\sum_{k=1}^{N(r)}\exp\left(\begin{array}{c}-\mu_{a1}\delta_{k1}(R_1)-\\ \mu_{a2}\delta_{k2}(R_1)-\\ \mu_{a3}\delta_{k3}(R_1)\end{array}\right)\right] = \\ \quad \mu_{a1}L_1(R_1) + \mu_{a2}L_2(R_1) + \mu_{a3}L_3(R_1) \\ N(R_2)\ln\left[\frac{I_{in}}{N_{in}}\frac{1}{I(R_2)}\sum_{k=1}^{N(r)}\exp\left(\begin{array}{c}-\mu_{a1}\delta_{k1}(R_2)-\\ \mu_{a2}\delta_{k2}(R_2)-\\ \mu_{a3}\delta_{k3}(R_2)\end{array}\right)\right] = \\ \quad \mu_{a1}L_1(R_2) + \mu_{a2}L_2(R_2) + \mu_{a3}L_3(R_2) \\ N(R_3)\ln\left[\frac{I_{in}}{N_{in}}\frac{1}{I(R_3)}\sum_{k=1}^{N(r)}\exp\left(\begin{array}{c}-\mu_{a1}\delta_{k1}(R_3)-\\ \mu_{a2}\delta_{k2}(R_3)-\\ \mu_{a3}\delta_{k3}(R_3)\end{array}\right)\right] = \\ \quad \mu_{a1}L_1(R_3) + \mu_{a2}L_2(R_3) + \mu_{a3}L_3(R_3) \end{cases} \quad (8)$$

Specifically, the light absorption coefficients $\mu_{a1}$ to $\mu_{a3}$ (initial values) of each skin layer estimated in the step A11 are substituted in the left-hand side of the expression (8) to calculate the corrected values of the light absorption coefficients $\mu_{a1}$ to $\mu_{a3}$ of each skin layer. The corrected values are repeatedly calculated until the light absorption coefficient converges to a true value. Specifically, the calculation process that substitutes the latest corrected values in the left-hand side of the expression (8) to calculate the corrected values of the light absorption coefficients $\mu_{a1}$ to $\mu_{a3}$ of each skin layer is repeated until a given convergence condition is satisfied (step A15: No→step A13).

The convergence condition may be a condition whereby the difference between the preceding calculated value and the current calculated value is equal to or smaller than a given threshold value, or may be a condition whereby the difference between the preceding calculated value and the current calculated value is continuously equal to or smaller than a given threshold value a given number of times. Alternatively, the repeat count of the convergence calculations may be set in advance.

The repeated calculations using the expression (8) are stopped as described below. In the following description, a glucose aqueous solution is used as a simple model, and the glucose concentration in the glucose aqueous solution is measured using the measurement light having a wavelength of 1600 nm that is close to the absorption peak in the glucose absorption spectrum.

The blood glucose level measurement accuracy required for clinical practice is normally ±10 mg/dl. For example, the light absorption coefficient of water at a wavelength of 1600 nm is 0.7 per mm, and the light absorption coefficient of glucose at a wavelength of 1600 nm is 1.3 per mm. The volume fraction of the 10 mg/dl glucose aqueous solution is $6.2 \times 10^{-5}$.

The light absorption coefficient $\mu_a$ of the glucose aqueous solution is shown by the following expression (9).

$$\mu_a = \mu_{ag} c_{vg} + \mu_{aw} c_{vw} \qquad (9)$$

where, $\mu_{ag}$ is the absorption coefficient of glucose, $\mu_{aw}$ is the absorption coefficient of water, $c_{vg}$ is the volume fraction (volume concentration) of glucose, and $c_{vw}$ is the volume fraction (volume concentration) of water.

The light absorption coefficient of the glucose aqueous solution changes by about 0.000037 per mm when the glucose concentration changes by 10 mg/dl (calculated under the above conditions). Specifically, it is necessary to determine a change in absorption coefficient by ±0.000037 in order to quantitatively determine a change in glucose concentration by ±10 mg/dl. Therefore, it may be determined that convergence has occurred when the fifth decimal digit in the calculation result does not change over several to about 10 calculations.

When the control section 100 has determined that the convergence condition has been satisfied (step A15: Yes), the control section 100 stores the layer-basis light absorption coefficient that includes the corrected value of the light absorption coefficient of each skin layer calculated by the latest second estimation calculation process in the storage section 600 as the estimated light absorption coefficient distribution data 670 (step A17). The process is then performed on the next wavelength. When the control section 100 has performed the process in the steps A7 to A17 on each wavelength, the control section 100 terminates the loop A process (step A19).

The concentration calculation section 150 then performs a concentration calculation process (step A21). The concentration calculation section 150 stores the calculated concentration in the storage section 600 as the measured concentration data 680. The control section 100 displays the calculated concentration of glucose in the dermis on the display section 300 (step A23), and terminates the concentration measurement process.

3. Principle 3-1. Estimation of Light Absorption Coefficient Distribution

The expressions (5) and (6) used in the first estimation calculation process that estimates the light absorption coefficient distribution in the step A11 of the concentration measurement process illustrated in FIG. 7, and the expressions (7) and (8) used in the second estimation calculation process that estimates the light absorption coefficient distribution in the step A13 of the concentration measurement process illustrated in FIG. 7, are derived as described below.

Scattered light (that is obtained when the measurement light is incident on the biological object) that has passed through only a shallow area from the surface of skin is detected at a position close to the irradiation section 40, and scattered light that has reached a deep area from the surface of skin is detected at a position away from the irradiation section 40. Specifically, the intensity of scattered light detected at a different position includes absorption information within the optical path distribution that corresponds to the detection position. Therefore, the light absorption coefficient spatial distribution can be estimated using an inverse problem solution technique by simulating or measuring the optical path that corresponds to each detection position of the space-resolved waveform in advance. Based on the above principle, the internal absorption distribution is reconstructed based on the space-resolved waveform of scattered light from the scattering object, and the substance concentration is calculated from the absorption distribution.

Light incident on the biological object from the irradiation section 40 propagates while repeating a scattering process, and is received by the light-receiving section 50. It is considered that the light that has reached the light-receiving section 50 has selectively passed through a local area (each layer) of the biological object corresponding to the detection position. The propagation path of photons in the biological object is characterized by the scattering coefficient, and a change in light intensity along the optical path is characterized by the light absorption coefficient.

The received light intensity I(r) of scattered light received at a position away from the irradiation position by the distance r is shown by the following expression (10) (normalized using the incident light intensity $I_{in}$) using the light intensity $i_k(r)$ (i.e., the incident intensity of a kth photon received at a position of the space-resolved waveform that corresponds to the distance r), the number $N_{in}$ of incident photons, and the number N(r) of photons (light intensity) received at the above position.

$$\frac{I(r)}{I_{in}} = \frac{1}{N_{in}} \sum_{k=1}^{N(r)} i_k(r) \qquad (10)$$

Note that the term "photon" used herein does not refer to a single quantum photon, but refers to a photon flux having energy that continuously attenuates.

The light intensity $i_k(r)$ is shown by the following expression (11) as the sum of the microscopic Beer-Lambert law.

$$i_k(r) = \exp(-\mu_a l) \qquad (11)$$

where, l is the moving distance of a photon in the biological object.

A case where the light absorption coefficient in the biological object differs in layers is discussed below. When the total numbers of layers is referred to as "M", the light absorption coefficient in the mth layer is referred to as "$\mu_{am}$", and the travel distance of the kth photon in each layer is referred to as "$l_{km}$", the expression (11) can be rewritten as shown by the following expression (12).

$$i_k(r) = \exp\left(-\sum_{m=1}^{M} \mu_{am} l_{km}\right) \qquad (12)$$

The following expression (13) is derived from the expressions (10) and (12).

$$\frac{I(r)}{I_{in}} = \frac{1}{N_{in}} \sum_{k=1}^{N(r)} \exp\left(-\sum_{m=1}^{M} \mu_{am} l_{km}\right) \quad (13)$$

When a variation in propagation path of each detected photon is taken into consideration, the space-resolved waveform I(r) of the detected scattered light intensity is shown by the following expression (14) by introducing the difference $\delta_{km}(r)$ between the average value $L_m'(r)$ of the propagation distance of each photon (received at a position that corresponds to the distance r) in the mth layer and the propagation distance $l_{km}(r)$ of the kth photon (received at a position that corresponds to the distance r) in the mth layer.

$$I(r) = \frac{I_{in}}{N_{in}} \sum_{k=1}^{N(r)} \exp\left[-\sum_{m=1}^{M} \mu_{am}(L_m'(r) + \delta_{km}(r))\right] = \quad (14)$$

$$\frac{I_{in}}{N_{in}} \sum_{k=1}^{N(r)} \exp\left[-\sum_{m=1}^{M} \mu_{am} L_m'(r) - \sum_{m=1}^{M} \mu_{am} \delta_{km}(r)\right]$$

Transforming the expression (14) yields the following expression (15), and thus yields the following expression (16).

$$I(r) = \frac{I_{in}}{N_{in}} \sum_{k=1}^{N(r)} \exp\left[-\sum_{m=1}^{M} \mu_{am}(L_m'(r) + \delta_{km}(r))\right] \quad (15)$$

$$= \frac{I_{in}}{N_{in}} \sum_{k=1}^{N(r)} \exp\left[-\sum_{m=1}^{M} \mu_{am} L_m'(r) - \sum_{m=1}^{M} \mu_{am} \delta_{km}(r)\right]$$

$$= \frac{I_{in}}{N_{in}} \sum_{k=1}^{N(r)} \left\{\exp\left(-\sum_{m=1}^{M} \mu_{am} L_m'(r)\right) \exp\left(-\sum_{m=1}^{M} \mu_{am} \delta_{km}(r)\right)\right\}$$

$$= \frac{I_{in}}{N_{in}} \exp\left(-\sum_{m=1}^{M} \mu_{am} L_m'(r)\right) \sum_{k=1}^{N(r)} \exp\left(-\sum_{m=1}^{M} \mu_{am} \delta_{km}(r)\right)$$

$$\ln\left[\frac{I_{in}}{N_{in}} \cdot \frac{1}{I(r)} \sum_{k=1}^{N(r)} \exp\left(-\sum_{m=1}^{M} \mu_{am} \delta_{km}(r)\right)\right] = \sum_{m=1}^{M} \mu_{am} L_m'(r) \quad (16)$$

where, $\delta_{km}(r)$ is the degree of variation in propagation optical path length of each photon in each layer (see the expression (3)).

The average value $L_m'(r)$ is shown by the expression (4) using the sum $L_m(r)$ of the number N(r) of the detected photons that have propagated in the mth layer (=optical path length distribution).

Therefore, the expression (7) used in the second estimation calculation process is obtained by rewriting the expression (16) using the sum $L_m(r)$. The expression (8) is obtained by applying the expression (7) to the three-layer structure of skin.

The expressions (5) and (6) used in the first estimation calculation process are derived as described below.

The following expression (19) is derived by the Taylor expansion of the exp function (see the following expression (18)) of the expression (14) from the Taylor expansion formula (see the following expression (17)).

$$f(x) = \sum_{n=0}^{\infty} \left\{\frac{f^{(n)}(a)}{n!}(x-a)^n\right\} \quad (17)$$

$$x \leftarrow -\sum_{m=1}^{M} \mu_{am} L_m'(r) - \sum_{m=1}^{M} \mu_{am} \delta_{km}(r), \quad (18)$$

$$a \leftarrow -\sum_{m=1}^{M} \mu_{am} L_m'(r)$$

$$I(r) = \frac{I_{in}}{N_{in}} \sum_{k=1}^{N(r)} \left\{ \begin{array}{l} \frac{1}{0!}\exp\left(-\sum_{m=1}^{M} \mu_{am} L_m'(r)\right) + \\ \frac{1}{1!}\exp\left(-\sum_{m=1}^{M} \mu_{am} L_m'(r)\right)\left(-\sum_{m=1}^{M} \mu_{am} \delta_{km}(r)\right) + \\ \frac{1}{2!}\exp\left(-\sum_{m=1}^{M} \mu_{am} L_m'(r)\right)\left(-\sum_{m=1}^{M} \mu_{am} \delta_{km}(r)\right)^2 + \\ \frac{1}{3!}\exp\left(-\sum_{m=1}^{M} \mu_{am} L_m'(r)\right)\left(-\sum_{m=1}^{M} \mu_{am} \delta_{km}(r)\right)^3 + \ldots \end{array} \right\} \quad (19)$$

Simplifying the expression (19) yields the following expression (20).

$$I(r) = \frac{I_{in}}{N_{in}} \exp\left(-\sum_{m=1}^{M} \mu_{am} L_m'(r)\right) \left\{ \begin{array}{l} N(r) + \frac{1}{1!}\sum_{k=1}^{N(r)}\left(-\sum_{m=1}^{M} \mu_{am} \delta_{km}(r)\right) + \\ \frac{1}{2!}\sum_{k=1}^{N(r)}\left(-\sum_{m=1}^{M} \mu_{am} \delta_{km}(r)\right)^2 + \\ \frac{1}{3!}\sum_{k=1}^{N(r)}\left(-\sum_{m=1}^{M} \mu_{am} \delta_{km}(r)\right)^3 + \ldots \end{array} \right\} \quad (20)$$

Since the integration of $\delta_{km}(r)$ for the total photons is 0, the linear term of the expression (20) is 0 (see the following expression (21)).

$$\sum_{k=1}^{N(r)}\left(-\sum_{m=1}^{M} \mu_{am} \delta_{km}(r)\right) = \quad (21)$$

$$-\sum_{m=1}^{M}\sum_{k=1}^{N(r)} \mu_{am} \delta_{km}(r) = -\sum_{m=1}^{M} \mu_{am}\left(\sum_{k=1}^{N(r)} \delta_{km}(r)\right) = 0$$

The following expression (22) is obtained by approximation on the assumption that the quadratic or higher terms of the expression (21) are sufficiently small.

$$I(r) = \frac{I_{in}}{N_{in}} \exp\left(-\sum_{m=1}^{M} \mu_{am} L_m'(r)\right) N(r) \quad (22)$$

Simplifying the expression (22) while using "$L_m(r)$" (see the expression (4)) yields the expression (5). The expression (6) is obtained by applying the expression (5) to the three-layer structure of skin.

3-2. Calculation of Concentration

The concentration calculation method used in the concentration calculation process in the step A21 in FIG. 7 is described below. The four wavelengths selected in the step A1 are referred to as $\lambda_1$, $\lambda_2$, $\lambda_3$, and $\lambda_4$. The light absorption coefficient of the epidermis estimated for the wavelength $\lambda$ is referred to as "$\mu_{a1}(\lambda)$", the light absorption coefficient of the dermis estimated for the wavelength $\lambda$ is referred to as "$\mu_{a2}(\lambda)$", and the light absorption coefficient of the subcutis estimated for the wavelength $\lambda$ is referred to as "$\mu_{a3}(\lambda)$". In this case, the glucose concentration in the dermis of skin is calculated using the light absorption coefficients $\lambda_{a2}(\lambda_1)$, $\mu_{a2}(\lambda_2)$, $\mu_{a2}(\lambda_3)$, and $\mu_{a2}(\lambda_4)$ of the dermis estimated for the four wavelengths $\lambda_1$, $\lambda_2$, $\lambda_3$, and $\lambda_4$ among the layer-basis light absorption coefficients stored as the estimated light absorption coefficient distribution data 670.

When the total number of components is "N", the volume fraction $c_{vi}$ of each component is calculated by the following expression (23).

$$\mu_{a2} = \sum_i^N \mu_{ai} c_{vi} \quad (23)$$

The dermis contains water, proteins, lipids, and glucose as the main components (i.e., N=4). The following expression (24) is obtained by rewriting the expression (23) as a four-component expression. The volume fraction of water, proteins, lipids, and glucose is calculated using the expression (24).

$$\begin{cases} \mu_{a2}(\lambda_1) = \mu_{aw}(\lambda_1)c_{vw} + \mu_{ap}(\lambda_1)c_{vp} + \mu_{al}(\lambda_1)c_{vl} + \mu_{ag}(\lambda_1)c_{vg} \\ \mu_{a2}(\lambda_2) + \mu_{aw}(\lambda_2)c_{vw} + \mu_{ap}(\lambda_2)c_{vp} + \mu_{al}(\lambda_2)c_{vl} + \mu_{ag}(\lambda_2)c_{vg} \\ \mu_{a2}(\lambda_3) = \mu_{aw}(\lambda_3)c_{vw} + \mu_{ap}(\lambda_3)c_{vp} + \mu_{al}(\lambda_3)c_{vl} + \mu_{ag}(\lambda_3)c_{vg} \\ \mu_{a2}(\lambda_4) = \mu_{aw}(\lambda_4)c_{vw} + \mu_{ap}(\lambda_4)c_{vp} + \mu_{al}(\lambda_4)c_{vl} + \mu_{ag}(\lambda_4)c_{vg} \end{cases} \quad (24)$$

where, $\mu_{ai}$ is the light absorption coefficient of each component, and the suffix "i" is the sign of each component. Water is indicated by "w", proteins are indicated by "p", lipids are indicated by "p", and glucose is indicated by "g". Specifically, $\mu_{aw}$, $\mu_{ap}$, $\mu_{al}$, and $\mu_{ag}$ respectively indicate the light absorption coefficient of water, the light absorption coefficient of proteins, the light absorption coefficient of lipids, and the light absorption coefficient of glucose. The light absorption coefficient differs depending on the wavelength. The light absorption coefficients "$\mu_{aw}(\lambda_1)$ to $\mu_{aw}(\lambda_4)$", "$\mu_{ap}(\lambda_1)$ to $\mu_{ap}(\lambda_4)$", "$\mu al(\lambda_1)$ to $\mu_{al}(\lambda_4)$", and "$\mu_{ag}(\lambda_1)$ to $\mu_{ag}(\lambda_4)$" correspond to the four wavelengths $\lambda_1$, $\lambda_2$, $\lambda_3$, and $\lambda_4$. These values are stored in advance in the storage section 600 as the component absorption information data 660 (absorption information).

$c_{vi}$ is the volume fraction of each component, and the suffix "i" is the sign of each component (see above). Specifically, $c_{vw}$, $c_{vp}$, $c_{vl}$, and $c_{vg}$ respectively indicate the volume fraction of water, the volume fraction of proteins, the volume fraction of lipids, and the volume fraction of glucose. Each volume fraction is unknown. The above simultaneous equations can be solved using the light absorption coefficients $\mu_{a2}(\lambda_1)$, $\mu_{a2}(\lambda_2)$, $\mu_{a2}(\lambda_3)$, and $\mu_{a2}(\lambda_4)$ of the dermis (i=2) calculated for the four wavelengths $\lambda_1$, $\lambda_2$, $\lambda_3$, and $\lambda_4$, and the component absorption information. Therefore, the volume fractions $c_{vw}$, $c_{vp}$, $c_{vl}$, and $c_{vg}$ of the respective components can be calculated.

When the volume fractions $c_{vw}$, $c_{vp}$, $c_{vl}$, and $c_{vg}$ of the respective components have been calculated, the volume fraction is converted into weight volume concentration or the like according to a known conversion expression to calculate the concentration of each component in the dermis.

4. Advantageous Effects

The concentration measurement device 1 detects the received light intensity of scattered light from the biological object at a plurality of light-receiving positions that differ in distance from the irradiation position at which the measurement light is applied to the biological object. More specifically, the light-receiving sections 50 are provided on the contact surface of the probe 5 (that is brought into contact with the biological object) at a plurality of positions that differ in distance from the irradiation section 40, and scattered light from the biological object is received by the light-receiving sections 50. The received light intensity of the scattered light received by each light-receiving section 50 is detected by the detection section 80 that is linked to the light-receiving section 50 on a one-to-one basis.

The light absorption coefficient distribution estimation section 140 estimates the layer-basis light absorption coefficient using the received light intensity of the scattered light detected by each detection section 80, the layer-basis propagation optical path length model that specifies the propagation optical path length of each skin layer corresponding to the position of the light-receiving section, the zero-absorption scattered light intensity model that specifies the scattered light intensity corresponding to the position of the light-receiving section when absorption of light by skin is zero, and the layer-basis photon propagation optical path length variation model that specifies the degree of variation in propagation optical path length of each photon in each skin layer. The concentration calculation section 150 calculates the concentration of glucose in the dermis using the layer-basis light absorption coefficient estimated by the light absorption coefficient distribution estimation section 140.

The first estimation section 141 included in the light absorption coefficient distribution estimation section 140 performs the first estimation calculation process that estimates the light absorption coefficient distribution using the detected scattered light intensity (received light intensity) and the total optical path length (propagation optical path length) at an identical distance from the irradiation position, and the zero-absorption scattered light intensity (received light intensity when absorption of light is zero). Specifically, the layer-basis light absorption coefficient is estimated by solving the simultaneous equations shown by the expressions (5) and (6) using the detected scattered light intensity, the total optical path length, and the zero-absorption scattered light intensity corresponding to each light-receiving section distance.

The layer-basis light absorption coefficient estimated by the first estimation calculation process may be used to calculate the concentration. In the embodiments of the invention, however, the layer-basis light absorption coefficient is corrected according to a given calculation expression into which the degree of variation in propagation optical path length of each photon in each skin layer is introduced, and the concentration is calculated using the corrected value.

Specifically, the second estimation section 142 included in the light absorption coefficient distribution estimation section 140 performs the second estimation calculation that estimates the light absorption coefficient distribution using the layer-basis light absorption coefficient estimated by the first estimation section 141 and the degree of variation in propagation optical path length of each photon. The second estimation calculation corrects the light absorption coefficient distribution by performing repeated calculation according to the calculation expression shown by the expressions (7) and (8) using the light absorption coefficient distribution estimated by the first estimation section 141 as the initial value.

The calculation expression is derived based on the fact that the received light intensity I(r) of the scattered light received at a position away from the irradiation position by the distance r can be expressed using the degree variation $\delta_{km}(r)$ in propagation optical path length of each photon. Specifically, the calculation expression is derived based on the fact that the propagation optical path length of the measurement light that is subjected to absorption based on the layer-basis light absorption coefficient can be expressed using the degree of variation in propagation optical path length of each photon used for the simulation process. It may be considered that the calculation expression represents the relationship between the layer-basis propagation optical path length of skin, the layer-basis light absorption coefficient, and the degree of variation in propagation optical path length of each photon.

The layer-basis light absorption coefficient estimated by the first estimation calculation process can be brought close to the true value as much as possible by repeating the calculation process that corrects the layer-basis light absorption coefficient estimated by the first estimation calculation process while applying the layer-basis light absorption coefficient to the above relationship. It is possible to accurately calculate the concentration of glucose in the dermis by utilizing the layer-basis light absorption coefficient estimated as described above.

5. Light-Receiving Section Arrangement Example

Although the above embodiments have been described taking an example in which the number of light-receiving sections 50 (detection sections 80) is three, four or more light-receiving sections 50 may be provided. For example, photoreceivers may be disposed at a plurality of positions situated at an identical distance from the irradiation position, and the light-receiving sections 50 may be implemented using these photodetectors (photodetector group).

Figure 8:
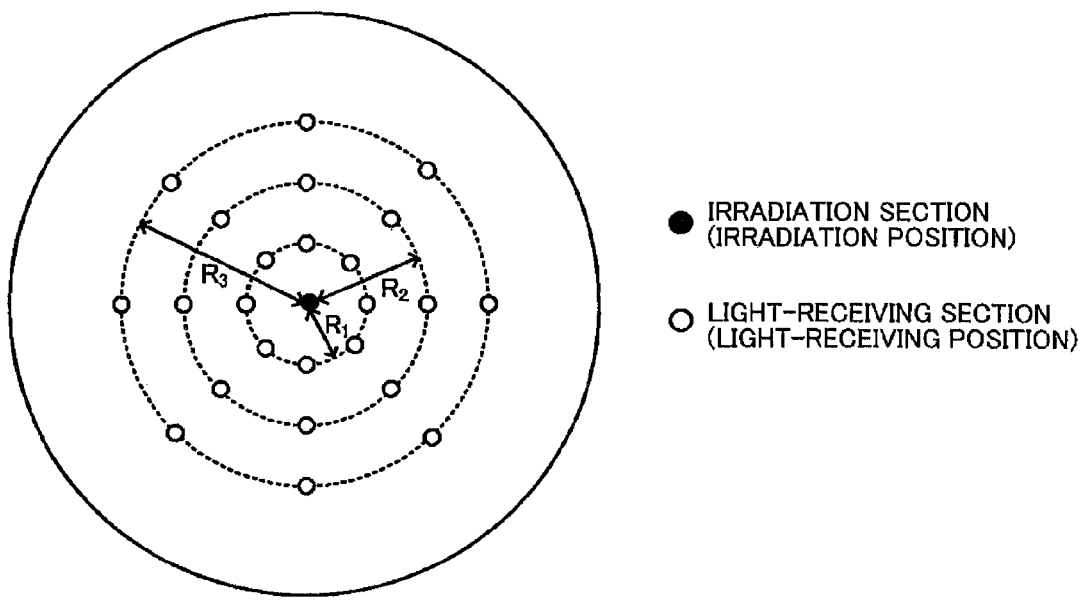
FIG. 8 is a view illustrating an example of the arrangement of light-receiving sections.

FIG. 8 is a view illustrating an example of the arrangement of the light-receiving section 50 that may be employed in such a case. FIG. 8 illustrates the contact surface of the probe 5. In FIG. 8, the black circle indicates the irradiation section 40 (irradiation position), and each white circle indicates the light-receiving section 50 (light-receiving position). For example, the irradiation section 40 may be provided at the center of the probe, and a plurality of light-receiving sections 50 may be provided concentrically around the irradiation section 40. In this case, it is effective to provide a given number of photoreceivers along each circumference. The number of photoreceivers provided along one circumference is referred to as "photoreceiver count".

For example, eight photoreceivers are provided at equal intervals along an identical circumference of a circle that is formed around the irradiation section 40 and has the light-receiving section distance R as radius. The eight photoreceivers are considered to be one photoreceiver group that corresponds to the light-receiving section distance R. Specifically, the light-receiving sections 50 corresponding to the light-receiving section distance R include the eight photoreceivers (photoreceiver group) that are provided along the circumference of a circle that is formed around the irradiation section 40 and has the radius R.

Light received by the photoreceivers that form one photoreceiver group is guided to one detector group by one scattered light guide group and one scattered light emitter group that are linked on a one-to-one basis. The intensity of the scattered light received by each photoreceiver is detected by the detector group. In this case, the detection sections 80 corresponding to the light-receiving section distance R detect eight received light intensities using eight detectors that form one detector group.

Figure 9:
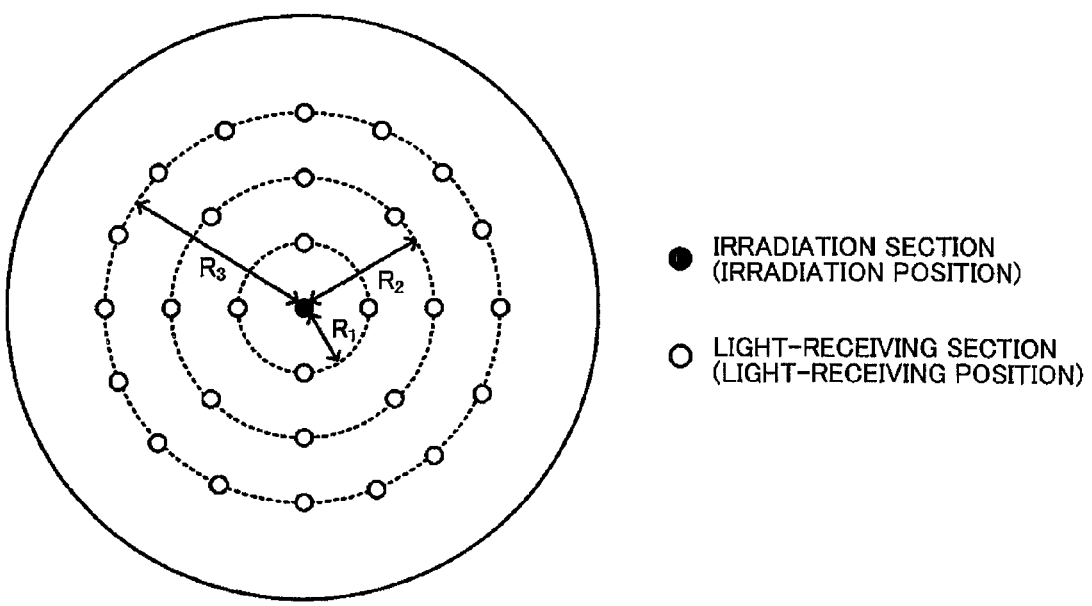
FIG. 9 is a view illustrating an example of the arrangement of light-receiving sections.

FIG. 9 is a view illustrating another arrangement example of the light-receiving sections 50. In the example illustrated in FIG. 9, a plurality of light-receiving sections 50 are provided concentrically around the irradiation section 40 in the same manner as in FIG. 8. In FIG. 9, however, a larger number of light-receiving sections 50 are provided along an identical circumference as the distance from the irradiation section 40 increases. Specifically, four photoreceivers are provided at equal intervals as the light-receiving sections 50 corresponding to the light-receiving section distance $R_1$, eight photoreceivers are provided at equal intervals as the light-receiving sections 50 corresponding to the light-receiving section distance $R_2$, and sixteen photoreceivers are provided at equal intervals as the light-receiving sections 50 corresponding to the light-receiving section distance $R_3$.

As illustrated in FIG. 4 (detected scattered light intensity waveform), the detected scattered light intensity I(R) tends to decrease as the light-receiving section distance R increases. The detected scattered light intensity significantly decreases, and it is difficult to determined the value when the distance from the irradiation position is equal to or longer than a given value. The scattered light-receiving sensitivity can be improved by receiving scattered light using a larger number of photoreceivers (i.e., increasing the light-receiving area) as the light-receiving section distance R increases, and detecting the received light intensity using the detection sections.

When employing the configuration illustrated in FIG. 8 or 9, the control section 100 acquires the detected scattered light intensities from the detector group corresponding to the photoreceiver group provided along an identical circumference. The control section 100 sums the acquired detected scattered light intensities to obtain a detected scattered light intensity sum value, and estimates the layer-basis light absorption coefficient by the above method using the detected scattered light intensity sum value.

When employing the configuration illustrated in FIG. 8 or 9, it is necessary to reflect the photoreceiver count in the simulation process performed by the simulation section 120. Specifically, the light-receiving section distance and the photoreceiver count (arrangement setting parameters) are specified as the light-receiving section setting data 620 stored in the storage section 600. The simulation section 120 refers to the light-receiving section setting data 620, and performs the Monte Carlo simulation process that reflects the arrangement setting parameters to generate the model data 630 (see FIG. 5).

Although the above embodiments have been described taking an example in which the light-receiving section 50 is provided on the contact surface of the probe 5, the light-receiving section 50 and the detection section 80 may be integrated. For example, the detection section 80 that is integrated with the light-receiving section 50 may be provided on the contact surface of the probe 5 when employing the configuration illustrated in FIG. 8 or 9.

Figure 10:
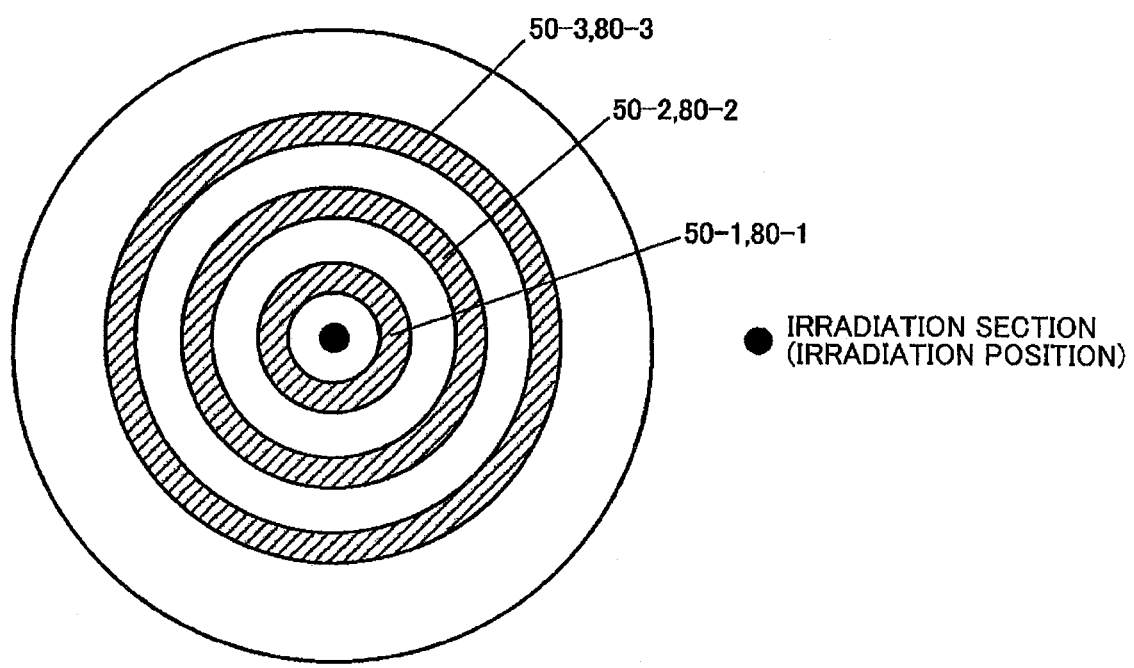
FIG. 10 is a view illustrating an example of the arrangement of light-receiving sections.

When using a light-receiving section that has a circular light-receiving surface (see FIG. 10), the circular light-receiving section 50 may be provided on the contact surface of the probe 5 around the irradiation section 40 (detection section 80), for example. In FIG. 10, each hatched area corresponds to the circular light-receiving section 50 (detection section 80). The distance from the irradiation section 40 to the center of the circular light-receiving section 50 corresponds to the light-receiving section distance R. A first light-receiving section 50-1 (first detection section 80-1), a second light-receiving section 50-2 (second detection section 80-2), and a third light-receiving section 50-3 (third detection section 80-3) are provided in this order from the irradiation section 40. The circular light-receiving section 50 receives scattered light from the biological object, and detects the received light intensity.

When employing the configuration illustrated in FIG. 10, the control section 100 acquires the scattered light intensity detected by the circular light-receiving section 50 (detection section 80) that has a given area (hereinafter referred to as "light-receiving section area"), and estimates the layer-basis light absorption coefficient by the above method using the detected scattered light intensity.

When employing the configuration illustrated in FIG. 10, it is necessary to reflect the photoreceiver count and the light-receiving section area in the simulation process performed by the simulation section 120. Specifically, the light-receiving section distance, the photoreceiver count, and the light-receiving section area (arrangement setting parameters) are specified as the light-receiving section setting data 620 stored in the storage section 600. The simulation section 120 refers to the light-receiving section setting data 620, and performs the Monte Carlo simulation process that reflects the arrangement setting parameters to generate the model data 630 (see FIG. 5).

6. Modifications

6-1. Application Example

Although the above embodiments have been described taking an example in which the subject is human skin, the subject is not limited thereto. For example, the light absorption coefficient distribution estimation device or the concentration measurement device according to the embodiments of the invention may be incorporated in a measurement system such as a sugar content measurement device that measures the sugar content in fruit. It is effective to estimate the light absorption coefficient distribution of a subject (e.g., layered substance) having a non-uniform (different) light absorption coefficient distribution using the light absorption coefficient distribution estimation device according to the embodiments of the invention.

The light absorption coefficient distribution estimation device may be used to measure the concentration of sugar (e.g., sucrose or lactose) other than glucose, or may be used to measure the concentration of each component in a solution (e.g., sodium chloride solution), for example. In the above embodiments, the concentrations of water, proteins, and lipids may be calculated in addition to the concentration of glucose.

6-2. Normalization Section

The above embodiments have been described taking an example in which the simulation section 120 performs the simulation process that reflects the arrangement setting parameters (e.g., light-receiving section distance, photoreceiver count, and light-receiving section area) to generate the model data 630. Note that the configuration described below may also be employed.

Specifically, the simulation section 120 may perform the simulation process on the assumption that the number of light-receiving sections is "1" or the area of the light-receiving section is "1 (or unit area)". In this case, the models of the propagation optical path length, the zero-absorption scattered light intensity, and the degree of variation in propagation optical path length per unit number and unit area of the light-receiving section 50 are calculated.

The control section 100 may normalize the scattered light intensity detected by the detection section 80 based on the arrangement setting parameters, and estimate the layer-basis light absorption coefficient using the normalized detected scattered light intensity when calculating the concentration. In this case, a normalization section that normalizes the received light intensity of the scattered light may be added as a functional section of the control section 100.

For example, when a given number (photoreceiver count) of photoreceivers are provided along an identical circumference as the light-receiving sections 50 (see FIG. 8 or 9), the scattered light intensities detected by the detector group corresponding to the photoreceiver group that forms the light-receiving sections 50 are summed to calculate the detected scattered light intensity sum value. The detected scattered light intensity sum value is converted/normalized into the detected scattered light intensity per photoreceiver by dividing the detected scattered light intensity sum value by the photoreceiver count.

When using the light-receiving section 50 having a given area (light-receiving section area) (see FIG. 9), the scattered light intensity that has been received by the light-receiving section 50 and detected by the detection section 80 is converted/normalized into the detected scattered light intensity per unit area of the light-receiving section 50 by dividing the scattered light intensity by the light-receiving section area.

6-3. Number of Light-Receiving Sections

The number of light-receiving sections 50 may be four or more. In this case, the light absorption coefficient distribution is estimated using pieces of data in a number larger than the number of skin layers. Specifically, since the number of pieces of data used for calculations is larger than the number of unknowns, an over-determined state occurs. Therefore, it is preferable to estimate and calculate the light absorption coefficient distribution by performing the estimation calculation process that utilizes the least-square method using the calculation expression used in the first estimation calculation process and the second estimation calculation process that is used to estimate the light absorption coefficient distribution.

More specifically, the second estimation section 142 may perform the second estimation calculation process that estimates the light absorption coefficient distribution using the following integral expression (25) that is developed from the expression (7) instead of using the expression (7) (general expression) and the expression (8) (concrete expression). The following expression (26) is obtained by applying the expression (25) to the three-layer structure of skin.

$$\begin{cases} \int_{x1}^{x2} \ln\left[\frac{I_{in}}{N_{in}} \cdot \frac{1}{I(r)} \sum_{k=1}^{N(r)} \exp\left(-\sum_{m=1}^{M} \mu_{am}\delta_{km}(r)\right)\right] L'_1(r) dr = \\ \qquad \sum_{m=1}^{M} \mu_{am} \int_{x1}^{x2} L'_1(r) L'_m(r) dr \\ \int_{x1}^{x2} \ln\left[\frac{I_{in}}{N_{in}} \cdot \frac{1}{I(r)} \sum_{k=1}^{N(r)} \exp\left(-\sum_{m=1}^{M} \mu_{am}\delta_{am}(r)\right)\right] L'_2(r) dr = \\ \qquad \sum_{m=1}^{M} \mu_{am} \int_{x1}^{x2} L'_2(r) L'_m(r) dr \\ \qquad \vdots \\ \int_{x1}^{x2} \ln\left[\frac{I_{in}}{N_{in}} \cdot \frac{1}{I(r)} \sum_{k=1}^{N(r)} \exp\left(-\sum_{m=1}^{M} \mu_{am}\delta_{km}(r)\right)\right] L'_m(r) dr = \\ \qquad \sum_{m=1}^{M} \mu_{am} \int_{x1}^{x2} L'_m(r) L'_m(r) dr \end{cases} \quad (25)$$

$$\begin{cases} \int_{x1}^{x2} \ln\left[\frac{I_{in}}{N_{in}} \cdot \frac{1}{I(r)} \sum_{k=1}^{N(r)} \exp\left(-\sum_{m=1}^{3} \mu_{am}\delta_{km}(r)\right)\right] L'_1(r)dr = \\ \qquad\qquad \sum_{m=1}^{3} \mu_{am} \int_{x1}^{x2} L'_1(r)L'_m(r)dr \\ \int_{x1}^{x2} \ln\left[\frac{I_{in}}{N_{in}} \cdot \frac{1}{I(r)} \sum_{k=1}^{N(r)} \exp\left(-\sum_{m=1}^{3} \mu_{am}\delta_{km}(r)\right)\right] L'_1(r)dr = \\ \qquad\qquad \sum_{m=1}^{3} \mu_{am} \int_{x1}^{x2} L'_2(r)L'_m(r)dr \\ \int_{x1}^{x2} \ln\left[\frac{I_{in}}{N_{in}} \cdot \frac{1}{I(r)} \sum_{k=1}^{N(r)} \exp\left(-\sum_{m=1}^{3} \mu_{am}\delta_{km}(r)\right)\right] L'_3(r)dr = \\ \qquad\qquad \sum_{m=1}^{3} \mu_{am} \int_{x1}^{x2} L'_3(r)L'_m(r)dr \end{cases} \quad (26)$$

where, x1 and x2 are the start distance and the end distance of the integral interval, respectively. The light-receiving section distance of the light-receiving section 50 that is closest to the irradiation position and the light-receiving section distance of the light-receiving section 50 that is farthest from the irradiation position correspond to x1 and x2.

6-4. Calculation of Concentration

Although the above embodiments have been described taking an example in which the concentration of glucose is calculated using the light absorption coefficient estimated by the second estimation calculation process, the concentration of glucose may be calculated using the light absorption coefficient estimated by the first estimation calculation process, and the second estimation calculation process may be omitted.

The concentration of glucose may be calculated using the following expressions (27) and (28) that are based on the relationship between the molar extinction coefficient and the molar concentration instead of calculating the concentration of glucose using the expressions (23) and (24) that are based on the relationship between the light absorption coefficient and the volume fraction.

$$\mu_{a2} = \sum_{i}^{N} \varepsilon_i c_i \quad (27)$$

$$\begin{cases} \mu_{a2}(\lambda_1) = \varepsilon_w(\lambda_1)c_w + \varepsilon_p(\lambda_1)c_p + \varepsilon_l(\lambda_1)c_l + \varepsilon_g(\lambda_1)c_g \\ \mu_{a2}(\lambda_2) = \varepsilon_w(\lambda_2)c_w + \varepsilon_p(\lambda_2)c_p + \varepsilon_l(\lambda_2)c_l + \varepsilon_g(\lambda_2)c_g \\ \mu_{a2}(\lambda_3) = \varepsilon_w(\lambda_3)c_w + \varepsilon_p(\lambda_3)c_p + \varepsilon_l(\lambda_3)c_l + \varepsilon_g(\lambda_3)c_g \\ \mu_{a2}(\lambda_4) = \varepsilon_w(\lambda_4)c_w + \varepsilon_p(\lambda_4)c_p + \varepsilon_l(\lambda_4)c_l + \varepsilon_g(\lambda_4)c_g \end{cases} \quad (28)$$

The light absorption coefficient and the component concentration may be calculated using a method based on multivariate analysis (e.g., principal component analysis or partial least squares (PLS) analysis). More specifically, a calibration curve may be drawn from the measured value of a material having known properties using multivariate analysis, and the component concentration may be determined by comparing the measured value of an unknown measurement target with the calibration curve.

6-5. Arrangement of Light-Receiving Sections

The arrangement of the light-receiving sections 50 described above with reference to FIGS. 8 to 10 are merely examples, and another arrangement may also be employed.

Although FIGS. 8 to 10 illustrate examples in which a plurality of light-receiving sections 50 are provided concentrically around the irradiation section 40, a plurality of light-receiving sections 50 need not necessarily be provided concentrically as long as a plurality of light-receiving sections 50 are circularly provided to surround the irradiation section 40. A plurality of light-receiving sections 50 may be provided in the shape of an arc (e.g., a semicircle or a quarter of a circle). The light-receiving sections 50 may be provided spirally around the irradiation position.

Alternatively, the photoreceivers may be provided on the probe either linearly or in a grid-like manner. More specifically, the light-receiving section 50 (light-receiving device) formed by a line sensor or an area sensor may be provided on the probe. The line sensor or the area sensor may be provided to include the irradiation section 40, or may be provided at a position away from the irradiation section 40 (e.g., a given position near the irradiation section 40). In this case, the light-receiving sections 50 that are positioned at an identical distance from the irradiation section 40 may be considered to form one light-receiving section group.

6-6. Light Source

The light source described in connection with the above embodiments need not necessarily be a multi-wavelength light source. A plurality of light sources that respectively emit light having a single wavelength may be disposed as the light source. A white light source may be provided instead of the multi-wavelength light source. White light emitted from the white light source may be dispersed using a spectroscope (e.g., monochromator), and light having a given wavelength may be applied to the subject. The light source may be a light source that repeatedly emits light. In this case, the light intensity may be integrated by the detection section 80 for a given time, and the integrated light intensity may be output to the control section 100 together with the light detection signal.

6-7. Detection of Light Intensity

The light intensity may be detected by counting the number of photons via photon counting detection when the intensity of the measurement light is weak.

Although only some embodiments of the present invention have been described in detail above, those skilled in the art will readily appreciate that many modifications are possible in the embodiments without materially departing from the novel teachings and advantages of this invention. Accordingly, all such modifications are intended to be included within scope of this invention.

What is claimed is:

1. A light absorption coefficient distribution estimation device comprising:
    a probe including a plurality of first light-receiving sections positioned at a first distance from an irradiation position at which measurement light is applied to a subject, a plurality of second light-receiving sections positioned at a second distance from the irradiation position, and a plurality of third light-receiving sections positioned at a third distance from the irradiation position; and
    a control section configured to
        calculate a first received light intensity by normalizing intensity of light received by the first light-receiving sections based on a number of the first light-receiving sections,
        calculate a second received light intensity by normalizing intensity of light received by the second light-receiving sections based on a number of the second light-receiving sections, calculate a third received light intensity by normalizing intensity of light received by the first light-receiving sections based on a number of the third light-receiving sections, estimate a light absorption coefficient distribution of the subject using the first received light intensity, the second received light intensity, the third received light intensity, a propagation optical path length model that specifies a propagation optical path length on a basis of the first distance, the second distance and the third distance, and a first model that specifies the received light intensity on a basis of the first distance, the second distance and the third distance when absorption of light is at a predetermined value, and correct the light absorption coefficient distribution using a second model that specifies a degree of variation in propagation optical path length of a photon on a basis of the first distance, the second distance and the third distance.

2. The light absorption coefficient distribution estimation device as defined in claim 1, wherein the first light-receiving sections, the second light-receiving sections and the third light-receiving sections are provided concentrically around an irradiation section that applies the measurement light.

3. The light absorption coefficient distribution estimation device as defined in claim 1, wherein the first light-receiving section, the second light-receiving section and the third light-receiving section are formed by a line sensor or an area sensor.

4. A concentration measurement device comprising:

the light absorption coefficient distribution estimation device as defined in claim 1; and a concentration calculation section that calculates a concentration of a specific component in the subject using the light absorption coefficient distribution estimated by the light absorption coefficient distribution estimation section.

5. The light absorption coefficient distribution estimation device as defined in claim 1, wherein the first model is zero-absorption scattered light intensity model, and the predetermined value is zero.

6. The light absorption coefficient distribution estimation device as defined in claim 1, wherein the control section is configured to correct the light absorption coefficient distribution by obtaining the degree of variation at the first distance, the degree of variation at the second distance, and the degree of variation at the third distance by using the second model.

7. A light absorption coefficient distribution estimation method, executed by a computer including a processor, based on a received light intensity of light received by a probe that receives scattered light from a subject, to which measurement light is applied, the probe including a plurality of first light-receiving sections positioned at a first distance from an irradiation position at which the measurement light is applied to the subject, a plurality of second light-receiving sections positioned at a second distance from the irradiation position, and a plurality of third light-receiving sections positioned at a third distance from the irradiation position, the light absorption coefficient distribution estimation method comprising:

calculating, by the processor, a first received light intensity by normalizing intensity of light received by the first light-receiving sections based on a number of the first light-receiving sections;

calculating, by the processor, a second received light intensity by normalizing intensity of light received by the second light-receiving sections based on a number of the second light-receiving sections;

calculating, by the processor, a third received light intensity by normalizing intensity of light received by the first light-receiving sections based on a number of the third light-receiving sections;

estimating, by the processor, a light absorption coefficient distribution of the subject using the first received light intensity, the second received light intensity, the third received light intensity, a propagation optical path length model that specifies a propagation optical path length on a basis of the first distance, the second distance and the third distance, and a first model that specifies the received light intensity on a basis of the first distance, the second distance and the third distance when absorption of light is at a predetermined value; and correcting, by the processor, the light absorption coefficient distribution using a second model that specifies a degree of variation in propagation optical path length of a photon on a basis of the first distance, the second distance and the third distance.

\* \* \* \* \*